(12) United States Patent
Zelder et al.

(10) Patent No.: US 8,771,998 B2
(45) Date of Patent: Jul. 8, 2014

(54) PROCESS FOR THE PRODUCTION OF GAMMA-AMINOBUTYRIC ACID

(75) Inventors: Oskar Zelder, Speyer (DE); Weol Kyu Jeong, Gunsan (KR); Corinna Klopprogge, Mannheim (DE); Andrea Herold, Ketsch (DE); Hartwig Schröder, Nußloch (DE)

(73) Assignee: BASF SE, Ludwigshafen (DE)

( * ) Notice: Subject to any disclaimer, the term of this patent is extended or adjusted under 35 U.S.C. 154(b) by 416 days.

(21) Appl. No.: 12/918,241

(22) PCT Filed: Feb. 20, 2009

(86) PCT No.: PCT/EP2009/001225
§ 371 (c)(1),
(2), (4) Date: Aug. 18, 2010

(87) PCT Pub. No.: WO2009/103547
PCT Pub. Date: Aug. 27, 2009

(65) Prior Publication Data
US 2010/0324258 A1    Dec. 23, 2010

(30) Foreign Application Priority Data
Feb. 21, 2008 (EP) .................................. 08151744

(51) Int. Cl.
| | | |
|---|---|---|
| *C12P 13/00* | (2006.01) |
| *C12N 9/88* | (2006.01) |
| *C12N 1/20* | (2006.01) |
| *C12N 15/00* | (2006.01) |
| *C12P 19/34* | (2006.01) |
| *C08G 69/08* | (2006.01) |
| *C07H 21/04* | (2006.01) |
| *C07K 1/00* | (2006.01) |

(52) U.S. Cl.
USPC ... 435/128; 435/232; 435/252.32; 435/252.3; 435/320.1; 435/69.1; 435/91.1; 528/310; 536/23.1; 536/23.2; 530/350

(58) Field of Classification Search
USPC .............. 435/128, 232, 252.32, 252.3, 320.1, 435/69.1, 91.1; 528/310; 536/23.1, 23.2; 530/350
See application file for complete search history.

(56) References Cited

U.S. PATENT DOCUMENTS

2006/0275264 A1* 12/2006 Fitzsimons et al. .......... 424/93.2
2007/0118916 A1* 5/2007 Puzio et al. ................... 800/278
2009/0318593 A1* 12/2009 Stoll et al. ..................... 524/108

FOREIGN PATENT DOCUMENTS

| EP | 1 108 790 A2 | 6/2001 |
| WO | WO-02/38736 A2 | 5/2002 |
| WO | WO-02/01013 A2 | 12/2002 |
| WO | WO-2006/028298 A2 | 3/2006 |
| WO | WO-2006/070944 A2 | 7/2006 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Guo et al., Protein tolerance to random amino acid change. PNAS., 2004, vol. 101 (25): 9205-9210.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Park, K. B., et al., "Expression of Rice Glutamate Decarboxylase in *Bifidobacterium Longum* Enhances γ-Aminobutyric Acid Production", Biotechnology Letters, 2005, vol. 27, No. 21, pp. 1681-1684.
"EST493624 cSTS *Solanum tuberosum* cDNA Clone cSTS8N16 5' Sequence, mRNA Sequence", EMBL Database, Accession No. BG594946, Apr. 13, 2001.

(Continued)

*Primary Examiner* — Ganapathirama Raghu
(74) *Attorney, Agent, or Firm* — Drinker Biddle & Reath LLP

(57) ABSTRACT

The present invention relates to a novel method for the fermentative production of gamma-aminobutyric acid (GABA) by cultivating a recombinant microorganism expressing an enzyme having a glutamate decarboxylase activity. The present invention also relates to corresponding recombinant hosts, recombinant vectors, expression cassettes and nucleic acids suitable for preparing such hosts as well as to a method for preparing polyamides making use of GABA as obtained fermentative production.

21 Claims, 3 Drawing Sheets

(56) References Cited

OTHER PUBLICATIONS

Pearson, W. R., et al., "Improved Tools for Biological Sequence Comparison", Proc. Natl. Acad. Sci. U.S.A., 1988, vol. 85, pp. 2444-2448.

Narang, S. A., "Tetrahedron Report No. 140: DNA Synthesis", Tetrahedron, 1983, vol. 39, No. 1, pp. 3-22.

Itakura, K., et al "Synthesis and Use of Synthetic Oligonucleotides", Ann. Rev. Biochem., 1984, vol. 53, pp. 323-356.

Itakura, K., et al., "Expression in *Escherichia coli* of a Chemically Synthesized Gene for the Hormone Somatostatin", Science, 1977, vol. 198, pp. 1056-1063.

Ike, Y., et al., "Solid Phase Synthesis of Polynucleotides. VIII. Synthesis of Mixed Oligodeoxyribonucleotides by the Phosphotriester Solid Phase Method", Nucleic Acids Research, 1983, vol. 11, No. 2, pp. 477-488.

Arkin, A. P., et al., "An Algorithm for Protein Engineering: Simulations of Recursive Ensemble Mutagenesis", Proc. Natl. Acad. Sci. U.S.A., 1992, vol. 89, pp. 7811-7815.

Delagrave, S., et al., "Recursive Ensemble Mutagenesis", Protein Engineering, 1993, vol. 6, No. 3, pp. 327-331.

Higgins, D. G., et al., "Fast and Sensitive Multiple Sequence Alignments on a Microcomputer", Comput. Appl. Biosci., 1989, vol. 5, No. 2, pp. 151-153.

Chenna, R., et al., "Multiple Sequence Alignment with the Clustal Series of Programs", Nucleic Acids Research, 2003, vol. 31, No. 13, pp. 3497-3500.

"Chemical Synthesis of Oligonucleotides", in "Biochemistry", Voet, D., et al., eds., John Wiley & Sons, Inc., 1995, Chapter 28, Section 7, pp. 896-897.

"Analysis of Genomic DNA by Southern Hybridization", in "Molecular Cloning, A Laboratory Manual", Sambrook, J., et al., eds., Cold Spring Harbor Laboratory Press, 1989, Chapter 9, pp. 9.31-9.57.

"Section II. Hybridization with Radioactive Probes, Unit 6.3. Using DNA Fragments as Probes", in "Current Protocol in Molecular Biology", John Wiley & Sons, Inc., 1989, pp. 6.3.1-6.3.6.

Greasham, R., et al., "Design and Optimization of Growth Media", in "Applied Microbial Physiology, A Practical Approach", Rhodes, P. M. et al., eds., IRL Press, 1997, Chapter 3, pp. 53-73.

Gallego, P. P., et al., "A Role for Glutamate Decarboxylase During Tomato Ripening: The Characterisation of a cDNA Encoding a Putative Glutamate Decarboxylase with a Calmodulin-Binding Site", Plant Molecular Biology, 1995, vol. 27, pp. 1143-1151.

Zik, M., et al., "C-Terminal Residues of Plant Glutamate Decarboxylase Are Required for Oligomerization of a High-Molecular Weight Complex and for Activation by Calcium/Calmodulin", Biochimica et Biophysica Acta, 2006, vol. 1764, pp. 872-876.

Meile, L., et al., "Safety Assessment of Dairy Microorganisms: *Propionibacterium* and *Bifidobacterium*", International Journal of Food Microbiology, 2008, vol. 126, pp. 316-320.

* cited by examiner

SEQUENCE LISTING

```
<160> NUMBER OF SEQ ID NOS: 14

<210> SEQ ID NO 1
<211> LENGTH: 1666
<212> TYPE: DNA
<213> ORGANISM: Artificial sequence
<220> FEATURE:
<223> OTHER INFORMATION: GDC potato- tomato chimera
<220> FEATURE:
<221> NAME/KEY: promoter
<222> LOCATION: (1)..(192)
<220> FEATURE:
<221> NAME/KEY: CDS
<222> LOCATION: (193)..(1605)
<220> FEATURE:
<221> NAME/KEY: misc_feature
<222> LOCATION: (193)..(471)
<223> OTHER INFORMATION: tomato sequence
<220> FEATURE:
<221> NAME/KEY: misc_feature
<222> LOCATION: (472)..(1200)
<223> OTHER INFORMATION: potato sequence
<220> FEATURE:
<221> NAME/KEY: misc_feature
<222> LOCATION: (1201)..(1605)
<223> OTHER INFORMATION: tomato sequence
<220> FEATURE:
<221> NAME/KEY: terminator
<222> LOCATION: (1606)..(1666)

<400> SEQUENCE: 1
```

-continued

```
tagctgccaa ttattccggg cttgtgaccc gctacccgat aaataggtcg gctgaaaaat        60
ttcgttgcaa tatcaacaaa aaggcctatc attgggaggt gtcgcaccaa gtactttgc        120 gaagcgccat ctgacggatt ttcaaaagat gtatatgctc ggtgcggaaa cctacgaaag       180
gattttttac cc atg gtg ctg acc acc acc tcc atc cgc gat tcc gaa gaa      231
              Met Val Leu Thr Thr Thr Ser Ile Arg Asp Ser Glu Glu
                1               5                  10 tcc ctg cac tgc acc ttc gca tcc cgc tac gtg cag gaa cca ctg cca         279
Ser Leu His Cys Thr Phe Ala Ser Arg Tyr Val Gln Glu Pro Leu Pro
     15                  20                  25 aag ttc aag atc cca aag aag tcc atg cca aag gaa gca gca tac cag         327
Lys Phe Lys Ile Pro Lys Lys Ser Met Pro Lys Glu Ala Ala Tyr Gln
 30                  35                  40                  45 atc gtg aac gat gaa ctg atg ctg gat ggc aac cca cgc ctg aac ctg         375
Ile Val Asn Asp Glu Leu Met Leu Asp Gly Asn Pro Arg Leu Asn Leu
                 50                  55                  60 gca tcc ttc gtg tcc acc tgg atg gaa cca gaa tgc gat aag ctg atc         423
Ala Ser Phe Val Ser Thr Trp Met Glu Pro Glu Cys Asp Lys Leu Ile
             65                  70                  75 atg tcc tcc atc aac aag aac tac gtg gat atg gat gaa tac cca gtg         471
Met Ser Ser Ile Asn Lys Asn Tyr Val Asp Met Asp Glu Tyr Pro Val
         80                  85                  90 acc acc gaa ctg cag aac cgc tgc gtg aac atg ctg gca cac ctg ttc         519
Thr Thr Glu Leu Gln Asn Arg Cys Val Asn Met Leu Ala His Leu Phe
     95                 100                 105 cac gca cca gtg ggc gat gat gaa acc gca gtg ggc gtg ggc acc gtg         567
His Ala Pro Val Gly Asp Asp Glu Thr Ala Val Gly Val Gly Thr Val
110                 115                 120                 125 ggc tcc tcc gaa gca atc atg ctg gca ggc ctg gca ttc aag cgc aag         615
Gly Ser Ser Glu Ala Ile Met Leu Ala Gly Leu Ala Phe Lys Arg Lys
                130                 135                 140 tgg cag gca aag cgc aag gca gaa ggc aag cca ttc gat aag cca aac         663
Trp Gln Ala Lys Arg Lys Ala Glu Gly Lys Pro Phe Asp Lys Pro Asn
            145                 150                 155 atc gtg acc ggc gca aac gtg cag gtg tgc tgg gaa aag ttc gca cgc         711
Ile Val Thr Gly Ala Asn Val Gln Val Cys Trp Glu Lys Phe Ala Arg
        160                 165                 170 tac ttc gaa gtg gaa ctg aag gaa gtg aag ctg aag gaa ggc tac tac         759
Tyr Phe Glu Val Glu Leu Lys Glu Val Lys Leu Lys Glu Gly Tyr Tyr
    175                 180                 185 gtg atg gat cca gca aag gca gtg gaa atg gtg gat gaa aac acc atc         807
Val Met Asp Pro Ala Lys Ala Val Glu Met Val Asp Glu Asn Thr Ile
190                 195                 200                 205 tgc gtg gca gca atc ctg ggc tcc acc ctg acc ggc gaa ttc gaa gat         855
Cys Val Ala Ala Ile Leu Gly Ser Thr Leu Thr Gly Glu Phe Glu Asp
                210                 215                 220 gtg aag ctg ctg aac gaa ctg ctg acc aag aag aac aag gaa acc ggc         903
Val Lys Leu Leu Asn Glu Leu Leu Thr Lys Lys Asn Lys Glu Thr Gly
            225                 230                 235 tgg gat acc cca atc cac gtg gat gca gca tcc ggc ggc ttc atc gca         951
Trp Asp Thr Pro Ile His Val Asp Ala Ala Ser Gly Gly Phe Ile Ala
        240                 245                 250 cca ttc ctg tgg cca gat ctg gaa tgg gat ttc cgc ctg cca ctg gtg         999
Pro Phe Leu Trp Pro Asp Leu Glu Trp Asp Phe Arg Leu Pro Leu Val
    255                 260                 265 aag tcc atc aac gtg tcc ggc cac aag tac ggc ctg gtg tac gca ggc        1047
Lys Ser Ile Asn Val Ser Gly His Lys Tyr Gly Leu Val Tyr Ala Gly
270                 275                 280                 285
```

```
gtg ggc tgg gtg atc tgg cgc tcc aag gaa gat ctg cca gat gaa ctg    1095
Val Gly Trp Val Ile Trp Arg Ser Lys Glu Asp Leu Pro Asp Glu Leu
            290                 295                 300 gtg ttc cac atc aac tac ctg ggc tcc gat cag cca acc ttc acc ctg    1143
Val Phe His Ile Asn Tyr Leu Gly Ser Asp Gln Pro Thr Phe Thr Leu
            305                 310                 315 aac ttc tcc aag tcc tcc tac cag atc atc gca cag tac tac cag ttc    1191
Asn Phe Ser Lys Ser Ser Tyr Gln Ile Ile Ala Gln Tyr Tyr Gln Phe
            320                 325                 330 atc cgc ctg ggc ttc gaa ggc tac aag gat gtg atg aag aac tgc ctg    1239
Ile Arg Leu Gly Phe Glu Gly Tyr Lys Asp Val Met Lys Asn Cys Leu
            335                 340                 345 tcc aac gca aag gtg ctg acc gaa ggc atc acc aag atg ggc cgc ttc    1287
Ser Asn Ala Lys Val Leu Thr Glu Gly Ile Thr Lys Met Gly Arg Phe
350                 355                 360                 365 gat atc gtg tcc aag gat gtg ggc gtg cca gtg gtg gca ttc tcc ctg    1335
Asp Ile Val Ser Lys Asp Val Gly Val Pro Val Val Ala Phe Ser Leu
                370                 375                 380 cgc gat tcc tcc aag tac acc gtg ttc gaa gtg tcc gaa cac ctg cgc    1383
Arg Asp Ser Ser Lys Tyr Thr Val Phe Glu Val Ser Glu His Leu Arg
                385                 390                 395 cgc ttc ggc tgg atc gtg cca gca tac acc atg cca gat gca gaa        1431
Arg Phe Gly Trp Ile Val Pro Ala Tyr Thr Met Pro Asp Ala Glu
            400                 405                 410 cac atc gca gtg ctg cgc gtg gtg atc cgc gaa gat ttc tcc cac tcc    1479
His Ile Ala Val Leu Arg Val Val Ile Arg Glu Asp Phe Ser His Ser
            415                 420                 425 ctg gca gaa cgc ctg gtg tcc gat atc gaa aag atc ctg tcc gaa ctg    1527
Leu Ala Glu Arg Leu Val Ser Asp Ile Glu Lys Ile Leu Ser Glu Leu
430                 435                 440                 445 gat acc cag cca cca cgc ctg cca acc aag gca gtg cgc gtg acc gca    1575
Asp Thr Gln Pro Pro Arg Leu Pro Thr Lys Ala Val Arg Val Thr Ala
                450                 455                 460 gaa gaa gtg cgc gat gat aag ggc gat taa agttctgtga aaacaccgt       1625
Glu Glu Val Arg Asp Asp Lys Gly Asp
            465                 470 ggggcagttt ctgcttcgcg gtgttttta tttgtggggc a                       1666

<210> SEQ ID NO 2
<211> LENGTH: 470
<212> TYPE: PRT
<213> ORGANISM: Artificial sequence
<220> FEATURE:
<223> OTHER INFORMATION: Synthetic Construct

<400> SEQUENCE: 2

Met Val Leu Thr Thr Thr Ser Ile Arg Asp Ser Glu Glu Ser Leu His
1               5                   10                  15

Cys Thr Phe Ala Ser Arg Tyr Val Gln Glu Pro Leu Pro Lys Phe Lys
            20                  25                  30

Ile Pro Lys Lys Ser Met Pro Lys Glu Ala Ala Tyr Gln Ile Val Asn
        35                  40                  45

Asp Glu Leu Met Leu Asp Gly Asn Pro Arg Leu Asn Leu Ala Ser Phe
    50                  55                  60

Val Ser Thr Trp Met Glu Pro Glu Cys Asp Lys Leu Ile Met Ser Ser
65                  70                  75                  80

Ile Asn Lys Asn Tyr Val Asp Met Asp Glu Tyr Pro Val Thr Thr Glu
                85                  90                  95

Leu Gln Asn Arg Cys Val Asn Met Leu Ala His Leu Phe His Ala Pro
```

```
            100               105                110
Val Gly Asp Asp Glu Thr Ala Val Gly Val Thr Val Gly Ser Ser
        115                 120                125
Glu Ala Ile Met Leu Ala Gly Leu Ala Phe Lys Arg Lys Trp Gln Ala
        130                 135                140
Lys Arg Lys Ala Glu Gly Lys Pro Phe Asp Lys Pro Asn Ile Val Thr
145                 150                 155                160
Gly Ala Asn Val Gln Val Cys Trp Glu Lys Phe Ala Arg Tyr Phe Glu
                165                 170                175
Val Glu Leu Lys Glu Val Lys Leu Lys Glu Gly Tyr Tyr Val Met Asp
                180                 185                190
Pro Ala Lys Ala Val Glu Met Val Asp Glu Asn Thr Ile Cys Val Ala
                195                 200                205
Ala Ile Leu Gly Ser Thr Leu Thr Gly Glu Phe Glu Asp Val Lys Leu
        210                 215                220
Leu Asn Glu Leu Leu Thr Lys Lys Asn Lys Thr Gly Trp Asp Thr
225                 230                 235                240
Pro Ile His Val Asp Ala Ala Ser Gly Gly Phe Ile Ala Pro Phe Leu
                245                 250                255
Trp Pro Asp Leu Glu Trp Asp Phe Arg Leu Pro Leu Val Lys Ser Ile
                260                 265                270
Asn Val Ser Gly His Lys Tyr Gly Leu Val Tyr Ala Gly Val Gly Trp
                275                 280                285
Val Ile Trp Arg Ser Lys Glu Asp Leu Pro Asp Glu Leu Val Phe His
        290                 295                300
Ile Asn Tyr Leu Gly Ser Asp Gln Pro Thr Phe Thr Leu Asn Phe Ser
305                 310                 315                320
Lys Ser Ser Tyr Gln Ile Ala Gln Tyr Tyr Gln Phe Ile Arg Leu
                325                 330                335
Gly Phe Glu Gly Tyr Lys Asp Val Met Lys Asn Cys Leu Ser Asn Ala
                340                 345                350
Lys Val Leu Thr Glu Gly Ile Thr Lys Met Gly Arg Phe Asp Ile Val
                355                 360                365
Ser Lys Asp Val Gly Val Pro Val Val Ala Phe Ser Leu Arg Asp Ser
        370                 375                380
Ser Lys Tyr Thr Val Phe Glu Val Ser Glu His Leu Arg Arg Phe Gly
385                 390                 395                400
Trp Ile Val Pro Ala Tyr Thr Met Pro Pro Asp Ala Glu His Ile Ala
                405                 410                415
Val Leu Arg Val Val Ile Arg Glu Asp Phe Ser His Ser Leu Ala Glu
                420                 425                430
Arg Leu Val Ser Asp Ile Glu Lys Ile Leu Ser Glu Leu Asp Thr Gln
                435                 440                445
Pro Pro Arg Leu Pro Thr Lys Ala Val Arg Val Thr Ala Glu Glu Val
        450                 455                460
Arg Asp Asp Lys Gly Asp
465                 470

<210> SEQ ID NO 3
<211> LENGTH: 1509
<212> TYPE: DNA
<213> ORGANISM: Solanum lycopersicum
<220> FEATURE:
<221> NAME/KEY: CDS
<222> LOCATION: (1)..(1509)
```

<400> SEQUENCE: 3

```
atg gta tta aca acg acg tcg ata aga gat tca gaa gag agc ttg cac     48
Met Val Leu Thr Thr Thr Ser Ile Arg Asp Ser Glu Glu Ser Leu His
1               5                   10                  15 tgt aca ttt gca tca aga tat gta cag gaa cct tta cct aag ttc aaa     96
Cys Thr Phe Ala Ser Arg Tyr Val Gln Glu Pro Leu Pro Lys Phe Lys
                20                  25                  30 atg cct aaa aaa tcc atg ccg aaa gaa gca gct tat cag att gta aac    144
Met Pro Lys Lys Ser Met Pro Lys Glu Ala Ala Tyr Gln Ile Val Asn
            35                  40                  45 gac gag ctt atg ttg gat ggt aac ccc agg ttg aat tta gct tcc ttt    192
Asp Glu Leu Met Leu Asp Gly Asn Pro Arg Leu Asn Leu Ala Ser Phe
        50                  55                  60 gtt agc aca tgg atg gag ccc gag tgc gat aag ctc atc atg tca tcc    240
Val Ser Thr Trp Met Glu Pro Glu Cys Asp Lys Leu Ile Met Ser Ser
65                  70                  75                  80 att aat aaa aac tat gtc gac atg gat gag tat cct gtc acc act gaa    288
Ile Asn Lys Asn Tyr Val Asp Met Asp Glu Tyr Pro Val Thr Thr Glu
                85                  90                  95 ctt caa aat aga tgt gtt aac atg tta gca cat ctt ttc cat gcc ccg    336
Leu Gln Asn Arg Cys Val Asn Met Leu Ala His Leu Phe His Ala Pro
                100                 105                 110 gtt ggt gat gat gag act gca gtt gga gtt ggt aca gtg ggt tca tca    384
Val Gly Asp Asp Glu Thr Ala Val Gly Val Gly Thr Val Gly Ser Ser
            115                 120                 125 gag gca ata atg ctt gct ggc ctt gct ttc aaa cgc aaa tgg caa tcg    432
Glu Ala Ile Met Leu Ala Gly Leu Ala Phe Lys Arg Lys Trp Gln Ser
        130                 135                 140 aaa aga aaa gca gaa ggc aaa cct ttc gat aag cct aat ata gtc act    480
Lys Arg Lys Ala Glu Gly Lys Pro Phe Asp Lys Pro Asn Ile Val Thr
145                 150                 155                 160 gga gct aat gtg cag gtc tgc tgg gaa aaa ttt gca agg tat ttt gag    528
Gly Ala Asn Val Gln Val Cys Trp Glu Lys Phe Ala Arg Tyr Phe Glu
                165                 170                 175 gtt gag ttg aag gag gtg aaa cta aaa gaa gga tac tat gta atg gac    576
Val Glu Leu Lys Glu Val Lys Leu Lys Glu Gly Tyr Tyr Val Met Asp
                180                 185                 190 cct gcc aaa gca gta gag ata gtg gat gag aat aca ata tgt gtt gct    624
Pro Ala Lys Ala Val Glu Ile Val Asp Glu Asn Thr Ile Cys Val Ala
            195                 200                 205 gca atc ctt ggt tct act ctg act ggg gag ttt gag gat gtg aag ctc    672
Ala Ile Leu Gly Ser Thr Leu Thr Gly Glu Phe Glu Asp Val Lys Leu
        210                 215                 220 cta aac gag ctc ctt aca aaa aag aac aag gaa acc gga tgg gag aca    720
Leu Asn Glu Leu Leu Thr Lys Lys Asn Lys Glu Thr Gly Trp Glu Thr
225                 230                 235                 240 ccg att cat gtc gat gct gcg agt gga gga ttt att gct cct ttc ctc    768
Pro Ile His Val Asp Ala Ala Ser Gly Gly Phe Ile Ala Pro Phe Leu
                245                 250                 255 tgg cca gat ctt gaa tgg gat ttc cgt ttg cct ctt gtg aaa agt ata    816
Trp Pro Asp Leu Glu Trp Asp Phe Arg Leu Pro Leu Val Lys Ser Ile
                260                 265                 270 aat gtc agc ggt cac aag tat ggc ctt gta tat gct ggt gtc ggt tgg    864
Asn Val Ser Gly His Lys Tyr Gly Leu Val Tyr Ala Gly Val Gly Trp
            275                 280                 285 gtg ata tgg cgg agc aag gaa gac ttg ccc gat gaa ctc gtc ttt cat    912
Val Ile Trp Arg Ser Lys Glu Asp Leu Pro Asp Glu Leu Val Phe His
        290                 295                 300
```

```
ata aac tac ctt ggg tct gat cag cct act ttt act ctc aac ttc tct    960
Ile Asn Tyr Leu Gly Ser Asp Gln Pro Thr Phe Thr Leu Asn Phe Ser
305                 310                 315                 320 aaa ggt tcc tat caa ata att gca cag tat tat cag tta ata aga ctt   1008
Lys Gly Ser Tyr Gln Ile Ile Ala Gln Tyr Tyr Gln Leu Ile Arg Leu
        325                 330                 335 ggc ttt gag ggt tat aag aac gtc atg aag aat tgc tta tca aac gca   1056
Gly Phe Glu Gly Tyr Lys Asn Val Met Lys Asn Cys Leu Ser Asn Ala
                340                 345                 350 aaa gta cta aca gag gga atc aca aaa atg ggg cgg ttc gat att gtc   1104
Lys Val Leu Thr Glu Gly Ile Thr Lys Met Gly Arg Phe Asp Ile Val
            355                 360                 365 tct aag gat gtg ggt gtt cct gtt gta gca ttt tct ctc agg gac agc   1152
Ser Lys Asp Val Gly Val Pro Val Val Ala Phe Ser Leu Arg Asp Ser
370                 375                 380 agc aaa tat acg gta ttt gaa gta tct gag cat ctc aga aga ttt gga   1200
Ser Lys Tyr Thr Val Phe Glu Val Ser Glu His Leu Arg Arg Phe Gly
385                 390                 395                 400 tgg atc gtc cct gca tac aca atg cca ccg gat gct gaa cac att gct   1248
Trp Ile Val Pro Ala Tyr Thr Met Pro Pro Asp Ala Glu His Ile Ala
                405                 410                 415 gta ctg cgg gtt gtc att aga gag gat ttc agc cac agc cta gct gag   1296
Val Leu Arg Val Val Ile Arg Glu Asp Phe Ser His Ser Leu Ala Glu
            420                 425                 430 aga ctt gtt tct gac att gag aaa att ctg tca gag ttg gac aca cag   1344
Arg Leu Val Ser Asp Ile Glu Lys Ile Leu Ser Glu Leu Asp Thr Gln
435                 440                 445 cct cct cgt ttg ccc acc aaa gct gtc cgt gtc act gct gag gaa gtg   1392
Pro Pro Arg Leu Pro Thr Lys Ala Val Arg Val Thr Ala Glu Glu Val
450                 455                 460 cgt gat gac aag ggt gat ggg ctt cat cat ttt cac atg gat act gta   1440
Arg Asp Asp Lys Gly Asp Gly Leu His His Phe His Met Asp Thr Val
465                 470                 475                 480 gag act cag aaa gac att atc aaa cat tgg agg aaa atc gca ggg aag   1488
Glu Thr Gln Lys Asp Ile Ile Lys His Trp Arg Lys Ile Ala Gly Lys
                485                 490                 495 aag acc agc gga gtc tgc tag                                       1509
Lys Thr Ser Gly Val Cys
            500

<210> SEQ ID NO 4
<211> LENGTH: 502
<212> TYPE: PRT
<213> ORGANISM: Solanum lycopersicum

<400> SEQUENCE: 4

Met Val Leu Thr Thr Thr Ser Ile Arg Asp Ser Glu Glu Ser Leu His
1               5                   10                  15

Cys Thr Phe Ala Ser Arg Tyr Val Gln Glu Pro Leu Pro Lys Phe Lys
            20                  25                  30

Met Pro Lys Lys Ser Met Pro Lys Glu Ala Ala Tyr Gln Ile Val Asn
        35                  40                  45

Asp Glu Leu Met Leu Asp Gly Asn Pro Arg Leu Asn Leu Ala Ser Phe
    50                  55                  60

Val Ser Thr Trp Met Glu Pro Glu Cys Asp Lys Leu Ile Met Ser Ser
65                  70                  75                  80

Ile Asn Lys Asn Tyr Val Asp Met Asp Glu Tyr Pro Val Thr Thr Glu
                85                  90                  95

Leu Gln Asn Arg Cys Val Asn Met Leu Ala His Leu Phe His Ala Pro
```

```
              100                 105                 110
Val Gly Asp Asp Glu Thr Ala Val Gly Val Thr Val Gly Ser Ser
            115                 120                 125
Glu Ala Ile Met Leu Ala Gly Leu Ala Phe Lys Arg Lys Trp Gln Ser
130                 135                 140
Lys Arg Lys Ala Glu Gly Lys Pro Phe Asp Lys Pro Asn Ile Val Thr
145                 150                 155                 160
Gly Ala Asn Val Gln Val Cys Trp Glu Lys Phe Ala Arg Tyr Phe Glu
                165                 170                 175
Val Glu Leu Lys Glu Val Lys Leu Lys Glu Gly Tyr Tyr Val Met Asp
                180                 185                 190
Pro Ala Lys Ala Val Glu Ile Val Asp Glu Asn Thr Ile Cys Val Ala
                195                 200                 205
Ala Ile Leu Gly Ser Thr Leu Thr Gly Glu Phe Glu Asp Val Lys Leu
            210                 215                 220
Leu Asn Glu Leu Leu Thr Lys Lys Asn Lys Glu Thr Gly Trp Glu Thr
225                 230                 235                 240
Pro Ile His Val Asp Ala Ala Ser Gly Gly Phe Ile Ala Pro Phe Leu
                245                 250                 255
Trp Pro Asp Leu Glu Trp Asp Phe Arg Leu Pro Leu Val Lys Ser Ile
                260                 265                 270
Asn Val Ser Gly His Lys Tyr Gly Leu Val Tyr Ala Gly Val Gly Trp
            275                 280                 285
Val Ile Trp Arg Ser Lys Glu Asp Leu Pro Asp Glu Leu Val Phe His
            290                 295                 300
Ile Asn Tyr Leu Gly Ser Asp Gln Pro Thr Phe Thr Leu Asn Phe Ser
305                 310                 315                 320
Lys Gly Ser Tyr Gln Ile Ala Gln Tyr Tyr Gln Leu Ile Arg Leu
                325                 330                 335
Gly Phe Glu Gly Tyr Lys Asn Val Met Lys Asn Cys Leu Ser Asn Ala
                340                 345                 350
Lys Val Leu Thr Glu Gly Ile Thr Lys Met Gly Arg Phe Asp Ile Val
            355                 360                 365
Ser Lys Asp Val Gly Val Pro Val Val Ala Phe Ser Leu Arg Asp Ser
        370                 375                 380
Ser Lys Tyr Thr Val Phe Glu Val Ser Glu His Leu Arg Arg Phe Gly
385                 390                 395                 400
Trp Ile Val Pro Ala Tyr Thr Met Pro Pro Asp Ala Glu His Ile Ala
                405                 410                 415
Val Leu Arg Val Val Ile Arg Glu Asp Phe Ser His Ser Leu Ala Glu
                420                 425                 430
Arg Leu Val Ser Asp Ile Glu Lys Ile Leu Ser Glu Leu Asp Thr Gln
            435                 440                 445
Pro Pro Arg Leu Pro Thr Lys Ala Val Arg Val Thr Ala Glu Glu Val
        450                 455                 460
Arg Asp Asp Lys Gly Asp Gly Leu His His Phe His Met Asp Thr Val
465                 470                 475                 480
Glu Thr Gln Lys Asp Ile Ile Lys His Trp Arg Lys Ile Ala Gly Lys
                485                 490                 495
Lys Thr Ser Gly Val Cys
                500

<210> SEQ ID NO 5
```

```
<211> LENGTH: 1401
<212> TYPE: DNA
<213> ORGANISM: Escherichia coli
<220> FEATURE:
<221> NAME/KEY: CDS
<222> LOCATION: (1)..(1401)

<400> SEQUENCE: 5 atg gac cag aag ctg tta acg gat ttc cgc tca gaa cta ctc gat tca    48
Met Asp Gln Lys Leu Leu Thr Asp Phe Arg Ser Glu Leu Leu Asp Ser
1               5                   10                  15 cgt ttt ggc gca aag gcc att tct act atc gcg gag tca aaa cga ttt    96
Arg Phe Gly Ala Lys Ala Ile Ser Thr Ile Ala Glu Ser Lys Arg Phe
                20                  25                  30 ccg ctg cac gaa atg cgc gat gat gtc gca ttt cag att atc aat gat    144
Pro Leu His Glu Met Arg Asp Asp Val Ala Phe Gln Ile Ile Asn Asp
            35                  40                  45 gaa tta tat ctt gat ggc aac gct cgt cag aac ctg gcc act ttc tgc    192
Glu Leu Tyr Leu Asp Gly Asn Ala Arg Gln Asn Leu Ala Thr Phe Cys
        50                  55                  60 cag acc tgg gac gac gaa aac gtc cat aaa ttg atg gat ttg tcg atc    240
Gln Thr Trp Asp Asp Glu Asn Val His Lys Leu Met Asp Leu Ser Ile
65                  70                  75                  80 aat aaa aac tgg atc gac aaa gaa gaa tat ccg caa tcc gca gcc atc    288
Asn Lys Asn Trp Ile Asp Lys Glu Glu Tyr Pro Gln Ser Ala Ala Ile
                85                  90                  95 gac ctg cgt tgc gta aat atg gtt gcc gat ctg tgg cat gcg cct gcg    336
Asp Leu Arg Cys Val Asn Met Val Ala Asp Leu Trp His Ala Pro Ala
            100                 105                 110 ccg aaa aat ggt cag gcc gtt ggc acc aac acc att ggt tct tcc gag    384
Pro Lys Asn Gly Gln Ala Val Gly Thr Asn Thr Ile Gly Ser Ser Glu
        115                 120                 125 gcc tgt atg ctc ggc ggg atg gcg atg aaa tgg cgt tgg cgc aag cgt    432
Ala Cys Met Leu Gly Gly Met Ala Met Lys Trp Arg Trp Arg Lys Arg
    130                 135                 140 atg gaa gct gca ggc aaa cca acg gat aaa cca aac ctg gtg tgc ggt    480
Met Glu Ala Ala Gly Lys Pro Thr Asp Lys Pro Asn Leu Val Cys Gly
145                 150                 155                 160 ccg gta caa atc tgc tgg cat aaa ttc gcc cgc tac tgg gat gtg gag    528
Pro Val Gln Ile Cys Trp His Lys Phe Ala Arg Tyr Trp Asp Val Glu
                165                 170                 175 ctg cgt gag atc cct atg cgc ccc ggt cag ttg ttt atg gac ccg aaa    576
Leu Arg Glu Ile Pro Met Arg Pro Gly Gln Leu Phe Met Asp Pro Lys
            180                 185                 190 cgc atg att gaa gcc tgt gac gaa aac acc atc ggc gtg gtg ccg act    624
Arg Met Ile Glu Ala Cys Asp Glu Asn Thr Ile Gly Val Val Pro Thr
        195                 200                 205 ttc ggc gtg acc tac acc ggt aac tat gag ttc cca caa ccg ctg cac    672
Phe Gly Val Thr Tyr Thr Gly Asn Tyr Glu Phe Pro Gln Pro Leu His
    210                 215                 220 gat gcg ctg gat aaa ttc cag gcc gac acc ggt atc gac atc gac atg    720
Asp Ala Leu Asp Lys Phe Gln Ala Asp Thr Gly Ile Asp Ile Asp Met
225                 230                 235                 240 cac atc gac gct gcc agc ggt ggc ttc ctg gca ccg ttc gtc gcc ccg    768
His Ile Asp Ala Ala Ser Gly Gly Phe Leu Ala Pro Phe Val Ala Pro
                245                 250                 255 gat atc gtc tgg gac ttc cgc ctg ccg cgt gtg aaa tcg atc agt gct    816
Asp Ile Val Trp Asp Phe Arg Leu Pro Arg Val Lys Ser Ile Ser Ala
            260                 265                 270 tca ggc cat aaa ttc ggt ctg gct ccg ctg ggc tgc ggc tgg gtt atc    864
Ser Gly His Lys Phe Gly Leu Ala Pro Leu Gly Cys Gly Trp Val Ile
```

```
                        275                 280                 285
tgg cgt gac gaa gaa gcg ctg ccg cag gaa ctg gtg ttc aac gtt gac       912
Trp Arg Asp Glu Glu Ala Leu Pro Gln Glu Leu Val Phe Asn Val Asp
    290                 295                 300 tac ctg ggt ggt caa att ggt act ttt gcc atc aac ttc tcc cgc ccg       960
Tyr Leu Gly Gly Gln Ile Gly Thr Phe Ala Ile Asn Phe Ser Arg Pro
305                 310                 315                 320 gcg ggt cag gta att gca cag tac tat gaa ttc ctg cgc ctc ggt cgt      1008
Ala Gly Gln Val Ile Ala Gln Tyr Tyr Glu Phe Leu Arg Leu Gly Arg
                325                 330                 335 gaa ggc tat acc aaa gta cag aac gcc tct tac cag gtt gcc gct tat      1056
Glu Gly Tyr Thr Lys Val Gln Asn Ala Ser Tyr Gln Val Ala Ala Tyr
        340                 345                 350 ctg gcg gat gaa atc gcc aaa ctg ggg ccg tat gag ttc atc tgt acg      1104
Leu Ala Asp Glu Ile Ala Lys Leu Gly Pro Tyr Glu Phe Ile Cys Thr
            355                 360                 365 ggt cgc ccg gac gaa ggc atc ccg gcg gtt tgc ttc aaa ctg aaa gat      1152
Gly Arg Pro Asp Glu Gly Ile Pro Ala Val Cys Phe Lys Leu Lys Asp
370                 375                 380 ggt gaa gat ccg gga tac acc ctg tac gac ctc tct gaa cgt ctg cgt      1200
Gly Glu Asp Pro Gly Tyr Thr Leu Tyr Asp Leu Ser Glu Arg Leu Arg
            385                 390                 395                 400 ctg cgc ggc tgg cag gtt ccg gcc ttc act ctc ggc ggt gaa gcc acc      1248
Leu Arg Gly Trp Gln Val Pro Ala Phe Thr Leu Gly Gly Glu Ala Thr
                405                 410                 415 gac atc gtg gtg atg cgc att atg tgt cgt cgc ggc ttc gaa atg gac      1296
Asp Ile Val Val Met Arg Ile Met Cys Arg Arg Gly Phe Glu Met Asp
                    420                 425                 430 ttt gct gaa ctg ttg ctg gaa gac tac aaa gcc tcc ctg aaa tat ctc      1344
Phe Ala Glu Leu Leu Leu Glu Asp Tyr Lys Ala Ser Leu Lys Tyr Leu
                435                 440                 445 agc gat cac ccg aaa ctg cag ggt att gcc cag cag aac agc ttt aaa      1392
Ser Asp His Pro Lys Leu Gln Gly Ile Ala Gln Gln Asn Ser Phe Lys
    450                 455                 460 cac acc tga                                                          1401
His Thr
465

<210> SEQ ID NO 6
<211> LENGTH: 466
<212> TYPE: PRT
<213> ORGANISM: Escherichia coli

<400> SEQUENCE: 6

Met Asp Gln Lys Leu Leu Thr Asp Phe Arg Ser Glu Leu Leu Asp Ser
1               5                   10                  15

Arg Phe Gly Ala Lys Ala Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110
```

Pro Lys Asn Gly Gln Ala Val Gly Thr Asn Thr Ile Gly Ser Ser Glu
            115                 120                 125

Ala Cys Met Leu Gly Gly Met Ala Met Lys Trp Arg Trp Arg Lys Arg
130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
        435                 440                 445

Ser Asp His Pro Lys Leu Gln Gly Ile Ala Gln Gln Asn Ser Phe Lys
    450                 455                 460

His Thr
465

<210> SEQ ID NO 7
<211> LENGTH: 3092
<212> TYPE: DNA
<213> ORGANISM: Escherichia coli
<220> FEATURE:
<221> NAME/KEY: CDS
<222> LOCATION: (1)..(1398)
<223> OTHER INFORMATION: gadB
<220> FEATURE:

<221> NAME/KEY: CDS
<222> LOCATION: (1557)..(3089)
<223> OTHER INFORMATION: gadC

<400> SEQUENCE: 7

| | | | | | | | | | | | | | | | | |
|---|---|---|---|---|---|---|---|---|---|---|---|---|---|---|---|---|
| atg | gat | aag | aag | caa | gta | acg | gat | tta | agg | tcg | gaa | cta | ctc | gat | tca | 48 |
| Met | Asp | Lys | Lys | Gln | Val | Thr | Asp | Leu | Arg | Ser | Glu | Leu | Leu | Asp | Ser | |
| 1 | | | | 5 | | | | | 10 | | | | | 15 | | |
| cgt | ttt | ggt | gcg | aag | tct | att | tcc | act | atc | gca | gaa | tca | aaa | cgt | ttt | 96 |
| Arg | Phe | Gly | Ala | Lys | Ser | Ile | Ser | Thr | Ile | Ala | Glu | Ser | Lys | Arg | Phe | |
| | | | 20 | | | | | 25 | | | | | 30 | | | |
| ccg | ctg | cac | gaa | atg | cgc | gac | gat | gtc | gca | ttc | cag | att | atc | aat | gac | 144 |
| Pro | Leu | His | Glu | Met | Arg | Asp | Asp | Val | Ala | Phe | Gln | Ile | Ile | Asn | Asp | |
| | | 35 | | | | | 40 | | | | | 45 | | | | |
| gaa | tta | tat | ctt | gat | ggc | aac | gct | cgt | cag | aac | ctg | gcc | act | ttc | tgc | 192 |
| Glu | Leu | Tyr | Leu | Asp | Gly | Asn | Ala | Arg | Gln | Asn | Leu | Ala | Thr | Phe | Cys | |
| | 50 | | | | | 55 | | | | | 60 | | | | | |
| cag | acc | tgg | gac | gac | gaa | aat | gtc | cac | aaa | ttg | atg | gat | tta | tcc | att | 240 |
| Gln | Thr | Trp | Asp | Asp | Glu | Asn | Val | His | Lys | Leu | Met | Asp | Leu | Ser | Ile | |
| 65 | | | | | 70 | | | | | 75 | | | | | 80 | |
| aac | aaa | aac | tgg | atc | gac | aaa | gaa | gaa | tat | ccg | caa | tcc | gca | gcc | atc | 288 |
| Asn | Lys | Asn | Trp | Ile | Asp | Lys | Glu | Glu | Tyr | Pro | Gln | Ser | Ala | Ala | Ile | |
| | | | | 85 | | | | | 90 | | | | | 95 | | |
| gac | ctg | cgt | tgc | gta | aat | atg | gtt | gcc | gat | ctg | tgg | cat | gcg | cct | gcg | 336 |
| Asp | Leu | Arg | Cys | Val | Asn | Met | Val | Ala | Asp | Leu | Trp | His | Ala | Pro | Ala | |
| | | | 100 | | | | | 105 | | | | | 110 | | | |
| ccg | aaa | aat | ggt | cag | gcc | gtt | ggc | acc | aac | acc | att | ggt | tct | tcc | gag | 384 |
| Pro | Lys | Asn | Gly | Gln | Ala | Val | Gly | Thr | Asn | Thr | Ile | Gly | Ser | Ser | Glu | |
| | | 115 | | | | | 120 | | | | | 125 | | | | |
| gcc | tgt | atg | ctc | ggc | ggg | atg | gcg | atg | aaa | tgg | cgt | tgg | cgc | aag | cgt | 432 |
| Ala | Cys | Met | Leu | Gly | Gly | Met | Ala | Met | Lys | Trp | Arg | Trp | Arg | Lys | Arg | |
| | 130 | | | | | 135 | | | | | 140 | | | | | |
| atg | gaa | gct | gca | ggc | aaa | cca | acg | gat | aaa | cca | aac | ctg | gtg | tgc | ggt | 480 |
| Met | Glu | Ala | Ala | Gly | Lys | Pro | Thr | Asp | Lys | Pro | Asn | Leu | Val | Cys | Gly | |
| 145 | | | | | 150 | | | | | 155 | | | | | 160 | |
| ccg | gta | caa | atc | tgc | tgg | cat | aaa | ttc | gcc | cgc | tac | tgg | gat | gtg | gag | 528 |
| Pro | Val | Gln | Ile | Cys | Trp | His | Lys | Phe | Ala | Arg | Tyr | Trp | Asp | Val | Glu | |
| | | | | 165 | | | | | 170 | | | | | 175 | | |
| ctg | cgt | gag | atc | cct | atg | cgc | ccc | ggt | cag | ttg | ttt | atg | gac | ccg | aaa | 576 |
| Leu | Arg | Glu | Ile | Pro | Met | Arg | Pro | Gly | Gln | Leu | Phe | Met | Asp | Pro | Lys | |
| | | | 180 | | | | | 185 | | | | | 190 | | | |
| cgc | atg | att | gaa | gcc | tgt | gac | gaa | aac | acc | atc | ggc | gtg | gtg | ccg | act | 624 |
| Arg | Met | Ile | Glu | Ala | Cys | Asp | Glu | Asn | Thr | Ile | Gly | Val | Val | Pro | Thr | |
| | | 195 | | | | | 200 | | | | | 205 | | | | |
| ttc | ggc | gtg | acc | tac | act | ggt | aac | tat | gag | ttc | cca | caa | ccg | ctg | cac | 672 |
| Phe | Gly | Val | Thr | Tyr | Thr | Gly | Asn | Tyr | Glu | Phe | Pro | Gln | Pro | Leu | His | |
| | 210 | | | | | 215 | | | | | 220 | | | | | |
| gat | gcg | ctg | gat | aaa | ttc | cag | gcc | gat | acc | ggt | atc | gac | atc | gac | atg | 720 |
| Asp | Ala | Leu | Asp | Lys | Phe | Gln | Ala | Asp | Thr | Gly | Ile | Asp | Ile | Asp | Met | |
| 225 | | | | | 230 | | | | | 235 | | | | | 240 | |
| cac | atc | gac | gct | gcc | agc | ggt | ggc | ttc | ctg | gca | ccg | ttc | gtc | gcc | ccg | 768 |
| His | Ile | Asp | Ala | Ala | Ser | Gly | Gly | Phe | Leu | Ala | Pro | Phe | Val | Ala | Pro | |
| | | | | 245 | | | | | 250 | | | | | 255 | | |
| gat | atc | gtc | tgg | gac | ttc | cgc | ctg | ccg | cgt | gtg | aaa | tcg | atc | agt | gct | 816 |
| Asp | Ile | Val | Trp | Asp | Phe | Arg | Leu | Pro | Arg | Val | Lys | Ser | Ile | Ser | Ala | |
| | | | 260 | | | | | 265 | | | | | 270 | | | |
| tca | ggc | cat | aaa | ttc | ggt | ctg | gct | ccg | ctg | ggc | tgc | ggc | tgg | gtt | atc | 864 |
| Ser | Gly | His | Lys | Phe | Gly | Leu | Ala | Pro | Leu | Gly | Cys | Gly | Trp | Val | Ile | |
| | | 275 | | | | | 280 | | | | | 285 | | | | |
| tgg | cgt | gac | gaa | gaa | gcg | ctg | ccg | cag | gaa | ctg | gtg | ttc | aac | gtt | gac | 912 |

```
               Trp Arg Asp Glu Glu Ala Leu Pro Gln Glu Leu Val Phe Asn Val Asp
                   290                 295                 300 tac ctg ggt ggt caa att ggt act ttt gcc atc aac ttc tcc cgc ccg          960
Tyr Leu Gly Gly Gln Ile Gly Thr Phe Ala Ile Asn Phe Ser Arg Pro
305                 310                 315                 320 gcg ggt cag gta att gca cag tac tat gaa ttc ctg cgc ctc ggt cgt         1008
Ala Gly Gln Val Ile Ala Gln Tyr Tyr Glu Phe Leu Arg Leu Gly Arg
                325                 330                 335 gaa ggc tat acc aaa gta cag aac gcc tct tac cag gtt gcc gct tat         1056
Glu Gly Tyr Thr Lys Val Gln Asn Ala Ser Tyr Gln Val Ala Ala Tyr
        340                 345                 350 ctg gcg gat gaa atc gcc aaa ctg ggg ccg tat gag ttc atc tgt acg         1104
Leu Ala Asp Glu Ile Ala Lys Leu Gly Pro Tyr Glu Phe Ile Cys Thr
    355                 360                 365 ggt cgc ccg gac gaa ggc atc ccg gcg gtt tgc ttc aaa ctg aaa gat         1152
Gly Arg Pro Asp Glu Gly Ile Pro Ala Val Cys Phe Lys Leu Lys Asp
370                 375                 380 ggt gaa gat ccg gga tac acc ctg tat gac ctc tct gaa cgt ctg cgt         1200
Gly Glu Asp Pro Gly Tyr Thr Leu Tyr Asp Leu Ser Glu Arg Leu Arg
385                 390                 395                 400 ctg cgc ggc tgg cag gtt ccg gcc ttc act ctc ggc ggt gaa gcc acc         1248
Leu Arg Gly Trp Gln Val Pro Ala Phe Thr Leu Gly Gly Glu Ala Thr
                405                 410                 415 gac atc gtg gtg atg cgc att atg tgt cgt cgc ggc ttc gaa atg gac         1296
Asp Ile Val Val Met Arg Ile Met Cys Arg Arg Gly Phe Glu Met Asp
                420                 425                 430 ttt gct gaa ctg ttg ctg gaa gac tac aaa gcc tcc ctg aaa tat ctc         1344
Phe Ala Glu Leu Leu Leu Glu Asp Tyr Lys Ala Ser Leu Lys Tyr Leu
        435                 440                 445 agc gat cac ccg aaa ctg cag ggt att gcc caa cag aac agc ttt aaa         1392
Ser Asp His Pro Lys Leu Gln Gly Ile Ala Gln Gln Asn Ser Phe Lys
    450                 455                 460 cat acc tgataacgtt taacggtaac ggtgtcccga acgaacccg tttcgggaca           1448
His Thr
465 atttccaaag tctgttcact ggcattagca acggaaaata ttgttctgaa tacgcttcag       1508 aacaaaacag gtgcggttcc gacaggaata ccgttttagg gggataat atg gct aca        1565
                                                     Met Ala Thr tca gta cag aca ggt aaa gct aag cag ctc aca tta ctt gga ttc ttt         1613
Ser Val Gln Thr Gly Lys Ala Lys Gln Leu Thr Leu Leu Gly Phe Phe
470                 475                 480                 485 gcc ata acg gca tcg atg gta atg gct gtt tat gaa tac cct acc ttc         1661
Ala Ile Thr Ala Ser Met Val Met Ala Val Tyr Glu Tyr Pro Thr Phe
                490                 495                 500 gca aca tcg ggc ttt tca tta gtc ttc ttc ctg cta tta ggc ggg att         1709
Ala Thr Ser Gly Phe Ser Leu Val Phe Phe Leu Leu Leu Gly Gly Ile
        505                 510                 515 tta tgg ttt att ccc gtg gga ctt tgt gct gcg aaa atg gcc acc gtc         1757
Leu Trp Phe Ile Pro Val Gly Leu Cys Ala Ala Glu Met Ala Thr Val
    520                 525                 530 gac ggc tgg gaa gaa ggt ggt gtc ttc gcc tgg gta tca aat act ctg         1805
Asp Gly Trp Glu Glu Gly Gly Val Phe Ala Trp Val Ser Asn Thr Leu
535                 540                 545 ggg ccg aga tgg gga ttt gca gcg atc tca ttt ggc tat ctg caa atc         1853
Gly Pro Arg Trp Gly Phe Ala Ala Ile Ser Phe Gly Tyr Leu Gln Ile
                555                 560                 565
550 gcc att ggt ttt att ccg atg ctc tat ttc gtg tta ggg gca ctc tcc         1901
Ala Ile Gly Phe Ile Pro Met Leu Tyr Phe Val Leu Gly Ala Leu Ser
                570                 575                 580
```

```
tac atc ctg aaa tgg cca gcg ctg aat gaa gac ccc att acc aaa act      1949
Tyr Ile Leu Lys Trp Pro Ala Leu Asn Glu Asp Pro Ile Thr Lys Thr
            585                 590                 595 att gca gca ctc atc att ctt tgg gcg ctg gca tta acg cag ttt ggt      1997
Ile Ala Ala Leu Ile Ile Leu Trp Ala Leu Ala Leu Thr Gln Phe Gly
        600                 605                 610 ggc acg aaa tac acg gcg cga att gct aaa gtt ggc ttc ttc gcc ggt      2045
Gly Thr Lys Tyr Thr Ala Arg Ile Ala Lys Val Gly Phe Phe Ala Gly
    615                 620                 625 atc ctg tta cct gca ttt att ttg atc gca tta gcg gct att tat ctg      2093
Ile Leu Leu Pro Ala Phe Ile Leu Ile Ala Leu Ala Ala Ile Tyr Leu
630                 635                 640                 645 cac tcc ggt gcc ccc gtt gct atc gaa atg gat tcg aag acc ttc ttc      2141
His Ser Gly Ala Pro Val Ala Ile Glu Met Asp Ser Lys Thr Phe Phe
                650                 655                 660 cct gac ttc tct aaa gtg ggc acc ctg gta gta ttt gtt gcc ttc att      2189
Pro Asp Phe Ser Lys Val Gly Thr Leu Val Val Phe Val Ala Phe Ile
            665                 670                 675 ttg agt tat atg ggc gta gaa gca tcc gca acc cac gtc aat gaa atg      2237
Leu Ser Tyr Met Gly Val Glu Ala Ser Ala Thr His Val Asn Glu Met
        680                 685                 690 agc aac cca ggg cgc gac tat ccg ttg gct atg tta ctg ctg atg gtg      2285
Ser Asn Pro Gly Arg Asp Tyr Pro Leu Ala Met Leu Leu Leu Met Val
    695                 700                 705 gcg gca atc tgc tta agc tct gtt ggt ggt ttg tct att gcg atg gtc      2333
Ala Ala Ile Cys Leu Ser Ser Val Gly Gly Leu Ser Ile Ala Met Val
710                 715                 720                 725 att ccg ggt aat gaa atc aac ctc tcc gca ggg gta atg caa acc ttt      2381
Ile Pro Gly Asn Glu Ile Asn Leu Ser Ala Gly Val Met Gln Thr Phe
                730                 735                 740 acc gtt ctg atg tcc cat gtg gca cca gaa att gag tgg acg gtt cgc      2429
Thr Val Leu Met Ser His Val Ala Pro Glu Ile Glu Trp Thr Val Arg
            745                 750                 755 gtg atc tcc gca ctg ctg ttg ctg ggt gtt ctg gcg gaa atc gcc tcc      2477
Val Ile Ser Ala Leu Leu Leu Leu Gly Val Leu Ala Glu Ile Ala Ser
        760                 765                 770 tgg att gtt ggt cct tct cgc ggg atg tat gta aca gcg cag aaa aac      2525
Trp Ile Val Gly Pro Ser Arg Gly Met Tyr Val Thr Ala Gln Lys Asn
775                 780                 785 ctg ctg cca gcg gca ttc gct aaa atg aac aaa aat ggc gta ccg gta      2573
Leu Leu Pro Ala Ala Phe Ala Lys Met Asn Lys Asn Gly Val Pro Val
790                 795                 800                 805 acg ctg gtc att tcg cag ctg gtg att acg tct atc gcg ttg atc atc      2621
Thr Leu Val Ile Ser Gln Leu Val Ile Thr Ser Ile Ala Leu Ile Ile
                810                 815                 820 ctc acc aat acc ggt ggc ggt aac aac atg tcc ttc ctg atc gca ctg      2669
Leu Thr Asn Thr Gly Gly Gly Asn Asn Met Ser Phe Leu Ile Ala Leu
            825                 830                 835 gcg ctg acg gtg gtg att tat ctg tgt gct tat ttc atg ctg ttt att      2717
Ala Leu Thr Val Val Ile Tyr Leu Cys Ala Tyr Phe Met Leu Phe Ile
        840                 845                 850 ggc tac att gtg ttg gtt ctt aaa cat cct gac tta aaa cgc aca ttt      2765
Gly Tyr Ile Val Leu Val Leu Lys His Pro Asp Leu Lys Arg Thr Phe
    855                 860                 865 aat atc cct ggt ggt aaa ggg gtg aaa ctg gtc gtg gca att gtc ggt      2813
Asn Ile Pro Gly Gly Lys Gly Val Lys Leu Val Val Ala Ile Val Gly
870                 875                 880                 885 ctg ctg act tca att atg gcg ttt att gtt tcc ttc ctg ccg ccg gat      2861
Leu Leu Thr Ser Ile Met Ala Phe Ile Val Ser Phe Leu Pro Pro Asp
```

```
                        890                 895                 900
aac atc cag ggt gat tct acc gat atg tat gtt gaa tta ctg gtt gtt      2909
Asn Ile Gln Gly Asp Ser Thr Asp Met Tyr Val Glu Leu Leu Val Val
            905                 910                 915 agt ttc ctg gtg gta ctt gcc ctg ccc ttt att ctc tat gct gtt cat      2957
Ser Phe Leu Val Val Leu Ala Leu Pro Phe Ile Leu Tyr Ala Val His
        920                 925                 930 gat cgt aaa ggc aaa gca aat acc ggc gtc act ctg gag cca atc aac      3005
Asp Arg Lys Gly Lys Ala Asn Thr Gly Val Thr Leu Glu Pro Ile Asn
935                 940                 945 agt cag aac gca cca aaa ggt cac ttc ttc ctg cac ccg cgt gca cgt      3053
Ser Gln Asn Ala Pro Lys Gly His Phe Phe Leu His Pro Arg Ala Arg
950                 955                 960                 965 tca cca cac tat att gtg atg aat gac aag aaa cac taa                  3092
Ser Pro His Tyr Ile Val Met Asn Asp Lys Lys His
                970                 975

<210> SEQ ID NO 8
<211> LENGTH: 466
<212> TYPE: PRT
<213> ORGANISM: Escherichia coli

<400> SEQUENCE: 8

Met Asp Lys Lys Gln Val Thr Asp Leu Arg Ser Glu Leu Leu Asp Ser
1               5                   10                  15

Arg Phe Gly Ala Lys Ser Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Lys Arg
    130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
```

```
              260                 265                 270
Ser Gly His Lys Phe Gly Leu Ala Pro Leu Gly Cys Gly Trp Val Ile
            275                 280                 285

Trp Arg Asp Glu Glu Ala Leu Pro Gln Glu Leu Val Phe Asn Val Asp
290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
            325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
            355                 360                 365

Gly Arg Pro Asp Glu Gly Ile Pro Ala Val Cys Phe Lys Leu Lys Asp
            370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
                420                 425                 430

Phe Ala Glu Leu Leu Leu Glu Asp Tyr Lys Ala Ser Leu Lys Tyr Leu
            435                 440                 445

Ser Asp His Pro Lys Leu Gln Gly Ile Ala Gln Gln Asn Ser Phe Lys
450                 455                 460

His Thr
465

<210> SEQ ID NO 9
<211> LENGTH: 511
<212> TYPE: PRT
<213> ORGANISM: Escherichia coli

<400> SEQUENCE: 9

Met Ala Thr Ser Val Gln Thr Gly Lys Ala Lys Gln Leu Thr Leu Leu
1               5                   10                  15

Gly Phe Phe Ala Ile Thr Ala Ser Met Val Met Ala Val Tyr Glu Tyr
                20                  25                  30

Pro Thr Phe Ala Thr Ser Gly Phe Ser Leu Val Phe Phe Leu Leu Leu
            35                  40                  45

Gly Gly Ile Leu Trp Phe Ile Pro Val Gly Leu Cys Ala Ala Glu Met
        50                  55                  60

Ala Thr Val Asp Gly Trp Glu Glu Gly Val Phe Ala Trp Val Ser
65                  70                  75                  80

Asn Thr Leu Gly Pro Arg Trp Gly Phe Ala Ala Ile Ser Phe Gly Tyr
                85                  90                  95

Leu Gln Ile Ala Ile Gly Phe Ile Pro Met Leu Tyr Phe Val Leu Gly
            100                 105                 110

Ala Leu Ser Tyr Ile Leu Lys Trp Pro Ala Leu Asn Glu Asp Pro Ile
        115                 120                 125

Thr Lys Thr Ile Ala Ala Leu Ile Ile Leu Trp Ala Leu Ala Leu Thr
130                 135                 140

Gln Phe Gly Gly Thr Lys Tyr Thr Ala Arg Ile Ala Lys Val Gly Phe
145                 150                 155                 160
```

-continued

```
Phe Ala Gly Ile Leu Leu Pro Ala Phe Ile Leu Ala Leu Ala Ala
            165                 170                 175

Ile Tyr Leu His Ser Gly Ala Pro Val Ala Ile Glu Met Asp Ser Lys
        180                 185                 190

Thr Phe Phe Pro Asp Phe Ser Lys Val Gly Thr Leu Val Val Phe Val
    195                 200                 205

Ala Phe Ile Leu Ser Tyr Met Gly Val Glu Ala Ser Ala Thr His Val
210                 215                 220

Asn Glu Met Ser Asn Pro Gly Arg Asp Tyr Pro Leu Ala Met Leu Leu
225                 230                 235                 240

Leu Met Val Ala Ala Ile Cys Leu Ser Ser Val Gly Leu Ser Ile
                245                 250                 255

Ala Met Val Ile Pro Gly Asn Glu Ile Asn Leu Ser Ala Gly Val Met
            260                 265                 270

Gln Thr Phe Thr Val Leu Met Ser His Val Ala Pro Glu Ile Glu Trp
        275                 280                 285

Thr Val Arg Val Ile Ser Ala Leu Leu Leu Gly Val Leu Ala Glu
    290                 295                 300

Ile Ala Ser Trp Ile Val Gly Pro Ser Arg Gly Met Tyr Val Thr Ala
305                 310                 315                 320

Gln Lys Asn Leu Leu Pro Ala Ala Phe Ala Lys Met Asn Lys Asn Gly
                325                 330                 335

Val Pro Val Thr Leu Val Ile Ser Gln Leu Val Ile Thr Ser Ile Ala
            340                 345                 350

Leu Ile Ile Leu Thr Asn Thr Gly Gly Asn Asn Met Ser Phe Leu
        355                 360                 365

Ile Ala Leu Ala Leu Thr Val Val Ile Tyr Leu Cys Ala Tyr Phe Met
370                 375                 380

Leu Phe Ile Gly Tyr Ile Val Leu Val Leu Lys His Pro Asp Leu Lys
385                 390                 395                 400

Arg Thr Phe Asn Ile Pro Gly Gly Lys Gly Val Lys Leu Val Val Ala
                405                 410                 415

Ile Val Gly Leu Leu Thr Ser Ile Met Ala Phe Ile Val Ser Phe Leu
            420                 425                 430

Pro Pro Asp Asn Ile Gln Gly Asp Ser Thr Asp Met Tyr Val Glu Leu
        435                 440                 445

Leu Val Val Ser Phe Leu Val Val Leu Ala Leu Pro Phe Ile Leu Tyr
450                 455                 460

Ala Val His Asp Arg Lys Gly Lys Ala Asn Thr Gly Val Thr Leu Glu
465                 470                 475                 480

Pro Ile Asn Ser Gln Asn Ala Pro Lys Gly His Phe Phe Leu His Pro
                485                 490                 495

Arg Ala Arg Ser Pro His Tyr Ile Val Met Asn Asp Lys Lys His
            500                 505                 510
```

<210> SEQ ID NO 10
<211> LENGTH: 42
<212> TYPE: DNA
<213> ORGANISM: Artificial sequence
<220> FEATURE:
<223> OTHER INFORMATION: PCR Primer

<400> SEQUENCE: 10
ccgctcgagc ggcccaagct tcggtaaata cttataccgg ag                    42

```
<210> SEQ ID NO 11
<211> LENGTH: 41
<212> TYPE: DNA
<213> ORGANISM: Artificial sequence
<220> FEATURE:
<223> OTHER INFORMATION: PCR Primer

<400> SEQUENCE: 11
ctagtctaga ctagcccaag cttgtcgatc atcgcctgtt g                41

<210> SEQ ID NO 12
<211> LENGTH: 43
<212> TYPE: DNA
<213> ORGANISM: Artificial sequence
<220> FEATURE:
<223> OTHER INFORMATION: PCR Primer

<400> SEQUENCE: 12
ccgctcgagc ggcccaagct tcgtgataaa ttgcgtcaga aag              43

<210> SEQ ID NO 13
<211> LENGTH: 43
<212> TYPE: DNA
<213> ORGANISM: Artificial sequence
<220> FEATURE:
<223> OTHER INFORMATION: PCR Primer

<400> SEQUENCE: 13
ctagactagt ctagcccaag cttctcgaat ttggcttgca tcc              43

<210> SEQ ID NO 14
<211> LENGTH: 5091
<212> TYPE: DNA
<213> ORGANISM: Artificial sequence
<220> FEATURE:
<223> OTHER INFORMATION: Plasmide

<400> SEQUENCE: 14
tcgatttaaa tctcgagagg cctgacgtcg ggcccggtac cacgcgtcat atgactagtt      60
cggacctagg gatatcgtcg acatcgatgc tcttctgcgt taattaacaa ttgggatcct     120
ctagacccgg gatttaaatc gctagcgggc tgctaaagga agcggaacac gtagaaagcc     180
agtccgcaga aacggtgctg accccggatg aatgtcagct actgggctat ctggacaagg     240
gaaaacgcaa gcgcaaagag aaagcaggta gcttgcagtg gcttacatg gcgatagcta     300 gactgggcgg ttttatggac agcaagcgaa ccggaattgc cagctggggc gccctctggt     360
aaggttggga agccctgcaa agtaaactgg atggctttct tgccgccaag gatctgatgg     420
cgcaggggat caagatctga tcaagagaca ggatgaggat cgtttcgcat gattgaacaa     480
gatggattgc acgcaggttc tccggccgct gggtgagga ggctattcgg ctatgactgg     540
gcacaacaga caatcggctg ctctgatgcc gccgtgttcc ggctgtcagc gcaggggcgc     600
ccggttcttt ttgtcaagac cgacctgtcc ggtgccctga atgaactgca ggacgaggca     660
gcgcggctat cgtggctggc cacgacgggc gttccttgcg cagctgtgct cgacgttgtc     720
actgaagcgg gaagggactg gctgctattg ggcgaagtgc cggggcagga tctcctgtca     780
tctcaccttg ctcctgccga gaaagtatcc atcatggctg atgcaatgcg gcggctgcat     840
acgcttgatc cggctacctg cccattcgac caccaagcga acatcgcat cgagcgagca     900 cgtactcgga tggaagccgg tcttgtcgat caggatgatc tggacgaaga gcatcagggg     960
ctcgcgccag ccgaactgtt cgccaggctc aaggcgcgca tgcccgacgg cgaggatctc    1020
```

```
gtcgtgaccc atggcgatgc ctgcttgccg aatatcatgg tggaaaatgg ccgcttttct    1080
ggattcatcg actgtggccg gctgggtgtg gcggaccgct atcaggacat agcgttggct    1140
acccgtgata ttgctgaaga gcttggcggc gaatgggctg accgcttcct cgtgctttac    1200
ggtatcgccg ctcccgattc gcagcgcatc gccttctatc gccttcttga cgagttcttc    1260
tgagcgggac tctggggttc gaaatgaccg accaagcgac gcccaacctg ccatcacgag    1320
atttcgattc caccgccgcc ttctatgaaa ggttgggctt cggaatcgtt ttccgggacg    1380
ccggctggat gatcctccag cgcggggatc tcatgctgga gttcttcgcc cacgctagcg    1440
gcgcgccggc cggcccggtg tgaaataccg cacagatgcg taaggagaaa ataccgcatc    1500
aggcgctctt ccgcttcctc gctcactgac tcgctgcgct cggtcgttcg gctgcggcga    1560
gcggtatcag ctcactcaaa ggcggtaata cggttatcca gaatcaggg ataacgca    1620 ggaaagaaca tgtgagcaaa aggccagcaa aaggccagga accgtaaaaa ggccgcgttg    1680
ctggcgtttt tccataggct ccgcccccct gacgagcatc acaaaaatcg acgctcaagt    1740
cagaggtggc gaaacccgac aggactataa agataccagg cgtttccccc tggaagctcc    1800
ctcgtgcgct ctcctgttcc gaccctgccg cttaccggat acctgtccgc ctttctccct    1860
tcgggaagcg tggcgctttc tcatagctca cgctgtaggt atctcagttc ggtgtaggtc    1920
gttcgctcca agctgggctg tgtgcacgaa ccccccgttc agcccgaccg ctgcgcctta    1980
tccggtaact atcgtcttga gtccaacccg gtaagcacg acttatcgcc actggcagca    2040
gccactggta acaggattag cagagcgagg tatgtaggcg gtgctacaga gttcttgaag    2100
tggtggccta actacggcta cactagaagg acagtatttg gtatctgcgc tctgctgaag    2160
ccagttacct tcggaaaaag agttggtagc tcttgatccg gcaaacaaac caccgctggt    2220
agcggtggtt tttttgtttg caagcagcag attacgcgca gaaaaaagg atctcaagaa    2280 gatcctttga tcttttctac ggggtctgac gctcagtgga acgaaaactc acgttaaggg    2340
attttggtca tgagattatc aaaaaggatc ttcacctaga tccttttaaa ggccggccgc    2400
ggccgcgcaa agtcccgctt cgtgaaaatt ttcgtgccgc gtgattttcc gccaaaaact    2460
ttaacgaacg ttcgttataa tggtgtcatg accttcacga cgaagtacta aaattggccc    2520
gaatcatcag ctatggatct ctctgatgtc gcgctggagt ccgacgcgct cgatgctgcc    2580
gtcgatttaa aaacggtgat cggattttc gagctctcg atacgacgga cgcgccagca    2640
tcacgagact gggccagtgc cgcgagcgac ctagaaactc tcgtggcgga tcttgaggag    2700
ctggctgacg agctgcgtgc tcggccagcg ccaggaggac gcacagtagt ggaggatgca    2760
atcagttgcg cctactgcgg tggcctgatt cctccccggc ctgacccgcg aggacggcgc    2820
gcaaaatatt gctcagatgc gtgtcgtgcc gcagccagcc gcgagcgcgc caacaaacgc    2880
cacgccgagg agctggaggc ggctaggtcg caaatggcgc tggaagtgcg tcccccgagc    2940
gaaattttgg ccatggtcgt cacagagctg gaagcggcag cgagaattat cgcgatcgtg    3000
gcggtgcccg caggcatgac aaacatcgta atgccgcgt ttcgtgtgcc gtggccgccc    3060
aggacgtgtc agcgccgcca ccacctgcac cgaatcggca gcagcgtcgc gcgtcgaaaa    3120
agcgcacagg cggcaagaag cgataagctg cacgaatacc tgaaaaatgt tgaacgcccc    3180
gtgagcggta actcacaggg cgtcggctaa ccccccagtcc aaacctggga gaaagcgctc    3240
aaaaatgact ctagcggatt cacgagacat tgacacaccg gcctggaaat tttccgctga    3300
tctgttcgac acccatcccg agctcgcgct gcgatcacgt ggctggacga gcgaagaccg    3360
ccgcgaattc ctcgctcacc tgggcagaga aaatttccag ggcagcaaga cccgcgactt    3420
```

-continued

```
cgccagcgct tggatcaaag acccggacac ggagaaacac agccgaagtt ataccgagtt    3480
ggttcaaaat cgcttgcccg gtgccagtat gttgctctga cgcacgcgca gcacgcagcc    3540
gtgcttgtcc tggacattga tgtgccgagc caccaggccg gcgggaaaat cgagcacgta    3600
aaccccgagg tctacgcgat tttggagcgc tgggcacgcc tggaaaaagc gccagcttgg    3660
atcggcgtga atccactgag cgggaaatgc cagctcatct ggctcattga tccggtgtat    3720
gccgcagcag gcatgagcag cccgaatatg cgcctgctgg ctgcaacgac cgaggaaatg    3780
acccgcgttt tcggcgctga ccaggctttt tcacataggc tgagccgtgg ccactgcact    3840
ctccgacgat cccagccgta ccgctggcat gcccagcaca atcgcgtgga tcgcctagct    3900
gatcttatgg aggttgctcg catgatctca ggcacagaaa aacctaaaaa acgctatgag    3960
caggagtttt ctagcggacg ggcacgtatc gaagcggcaa gaaaagccac tgcggaagca    4020
aaagcacttg ccacgcttga agcaagcctg ccgagcgccg ctgaagcgtc tggagagctg    4080
atcgacggcg tccgtgtcct ctggactgct ccagggcgtg ccgcccgtga tgagacggct    4140
tttcgccacg ctttgactgt gggataccag ttaaaagcgg ctggtgagcg cctaaaagac    4200
accaagggtc atcgagccta cgagcgtgcc tacaccgtcg ctcaggcggt cggaggaggc    4260
cgtgagcctg atctgccgcc ggactgtgac cgccagacgg attggccgcg acgtgtgcgc    4320
ggctacgtcg ctaaaggcca gccagtcgtc cctgctcgtc agacagagac gcagagccag    4380
ccgaggcgaa aagctctggc cactatggga agacgtggcg gtaaaaaggc cgcagaacgc    4440
tggaaagacc caaacagtga gtacgcccga gcacagcgag aaaaactagc taagtccagt    4500
caacgacaag ctaggaaagc taaaggaaat cgcttgacca ttgcaggttg gtttatgact    4560
gttgagggag agactggctc gtggccgaca atcaatgaag ctatgtctga atttagcgtg    4620
tcacgtcaga ccgtgaatag agcacttaag gtctgcgggc attgaacttc cacgaggacg    4680
ccgaaagctt cccagtaaat gtgccatctc gtaggcagaa aacggttccc ccgtagggtc    4740
tctctcttgg cctcctttct aggtcgggct gattgctctt gaagctctct aggggggctc    4800
acaccatagg cagataacgt tccccaccgg ctcgcctcgt aagcgcacaa ggactgctcc    4860
caaagatctt caaagccact gccgcgactg ccttcgcgaa gccttgcccc gcggaaattt    4920
cctccaccga gttcgtgcac accccctatgc caagcttctt tcaccctaaa ttcgagagat    4980
tggattctta ccgtggaaat tcttcgcaaa aatcgtcccc tgatcgccct tgcgacgttg    5040
gcgtcggtgc cgctggttgc gcttggcttg accgacttga tcagcggccg c             5091
```

PROCESS FOR THE PRODUCTION OF GAMMA-AMINOBUTYRIC ACID

RELATED APPLICATIONS

This application is a national stage application (under 35 U.S.C. §371) of PCT/EP2009/001225, filed Feb. 20, 2009, which claims benefit of European application 08151744.3, filed Feb. 21, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13111_00155. The size of the text file is 64 KB, and the text file was created on Aug. 18, 2010.

The present invention relates to a novel method for the fermentative production of gamma-aminobutyric acid (GABA) by cultivating a recombinant microorganism expressing an enzyme having a glutamate decarboxylase activity. The present invention also relates to corresponding recombinant hosts, recombinant vectors, expression cassettes and nucleic acids suitable for preparing such hosts as well as to a method for preparing polyamides making use of GABA as obtained fermentative production.

BACKGROUND OF THE INVENTION

GABA (CAS number 56-12-2) is an important ubiquitous non-protein amino acid in both prokaryotic and eukaryotic organisms. It shows different biological functions, for example as representative depressive neurotransmitter in the sympathetic nervous system and it is effective for lowering the blood pressure of experimental animals and humans. The compound is synthesized by glutamate decarboxylase (GAD; EC 4.1.1.15) from glutamate.

GABA is used in different technical fields. For example, GABA-enriched food can be used as a dietary supplement and nutraceutical to help treat sleeplessness, depression and autonomic disorders, chronic alcohol-related symptoms, and to stimulate immune cells. The compound can also be used as a raw material for the production of polyamides and of pyrrolidone.

A suitable way for the fermentative production of said commercially interesting chemical compound has not yet been described.

The object of the present invention is, therefore, to provide a suitable method for the fermentative production of GABA or corresponding salts thereof.

SUMMARY OF THE INVENTION

Figure 1:
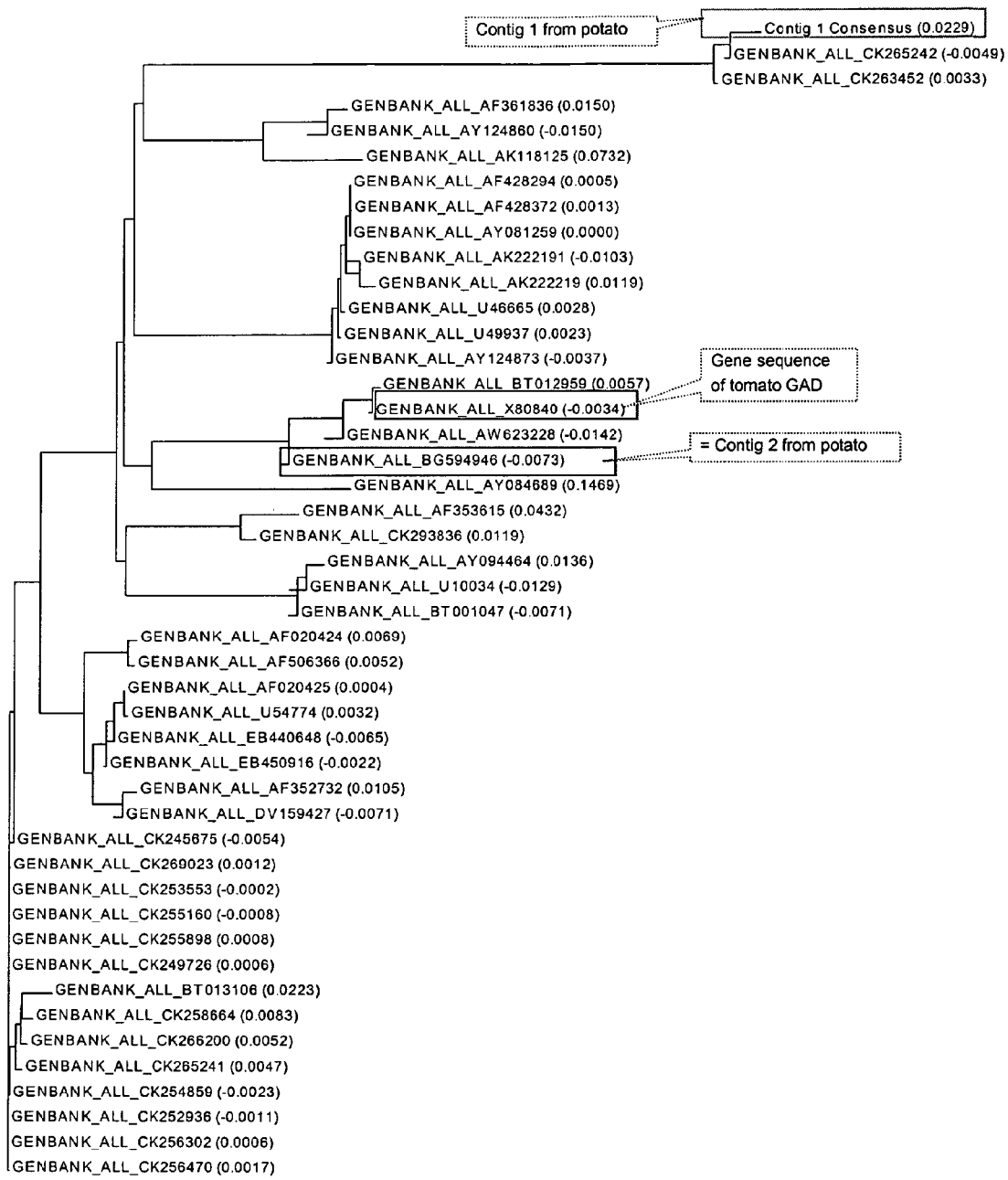
FIG. 1 depicts the comparison of contigs from potato ESTs with GAD homologs from plants.

The above-mentioned problem was solved by the present invention teaching the fermentative production of GABA or a salt thereof by cultivating a recombinant glutamate producing microorganism expressing GAD enzyme which enzyme converts glutamate that is formed in said microorganism to GABA.

DETAILED DESCRIPTION OF THE INVENTION

1. Preferred Embodiments

The present invention relates to a method for the fermentative production of gamma-aminobutyric acid (GABA), which method comprises the cultivation of a recombinant microorganism which microorganism preferably being derived from a parent microorganism having the ability to produce glutamate, and which recombinant microorganism, qualitatively or quantitatively, retains said ability of said parent microorganism, and additionally having the ability to express heterologous glutamate decarboxylase (E.C. 4.1.1.15), so that glutamate is converted to GABA; and optionally isolating GABA from the fermentation broth. Said modified microorganism also may or may not retain its ability to produce glutamate.

In particular, said microorganism is a glutamate producing bacterium, particularly a coryneform bacterium, like a bacterium of the genus *Corynebacterium*, as, for example, *Corynebacterium glutamicum*.

Said heterologous glutamate decarboxylase is of prokaryotic or eukaryotic origin.

In one specific embodiment, said heterologous glutamate decarboxylase is a plant glutamate decarboxylase or a chimeric glutamate decarboxylase comprising at least one amino acid sequence portion derived from plant glutamate decarboxylase. Said "at least one amino acid sequence portion derived from plant glutamate decarboxylase" comprises at least ten consecutive amino acid residues of said plant enzyme. In total, there may be 1 to 10, in particular, 1 to 5, preferably 1 or 2 amino acid sequence portions derived from said plant sequence. Each of said portions may have a length of 10 to 500, 10 to 450, 10 to 400, 20 to 350, 40 to 300, 50 to 250, 60 to 200, 70 to 150 or 80 to 100 consecutive amino acid residues of said plant enzyme.

In particular, said heterologous glutamate decarboxylase is a decarboxylase of a plant of the genus *Solanum*, in particular from *Solanum tuberosum*, i.e. potato. For example, said heterologous glutamate decarboxylase is from *Solanum tuberosum* and comprises an amino acid sequence from Thr94 to Leu336 of SEQ ID NO: 2 or a sequence having 80% to less than 100% identity thereto, as, for example, 85%, 90%, 91%, 92%, 93%, 94%, 95%, 96%, 97%, 98% or 99%.

In addition, said heterologous glutamate decarboxylase may be N-terminally and/or C-terminally supplemented by the corresponding terminal amino acid sequences of a glutamate decarboxylase from *Solanum tuberosum*, or N-terminally and/or or C-terminally supplemented by the corresponding terminal amino acid sequences of a glutamate decarboxylase of a second plant, different from *Solanum tuberosum*. For example, said second plant is *Solanum lycopersicum*, i.e. tomato.

In a particular embodiment, said glutamate decarboxylase comprises an amino acid sequence according to SEQ ID NO: 2 or a sequence having 80% to less than 100% identity thereto, as, for example, 85%, 90%, 91%, 92%, 93%, 94%, 95%, 96%, 97%, 98% or 99%.

According to another embodiment of the invention, said heterologous glutamate decarboxylase is a bacterial glutamate decarboxylase, for example from a bacterium of the genus *Escherichia*, in particular from *E. coli*. Said *E. coli* glutamate decarboxylase may be selected from GadA of SEQ ID NO:6, the GadBC complex comprising the GadB sequence of SEQ ID NO: 8 and the GadC sequence of SEQ ID NO: 9 and sequences having 80% to less than 100% identity to GadA or GadBC, respectively. Suitable sequences may have, for example, an identity of 85%, 90%, 91%, 92%, 93%, 94%, 95%, 96%, 97%, 98% or 99%

In another embodiment, the enzyme having glutamate decarboxylase activity is encoded by a nucleic acid sequence, which is adapted to the codon usage of said parent microorganism having the ability to produce glutamate.

In particular, the enzyme having glutamate decarboxylase activity may be encoded by a nucleic acid sequence comprising a coding sequence selected from a) position 472 to 1200 according to SEQ ID NO:1 or from position 193 to 1605 according to SEQ ID NO:1;
b) SEQ ID NO: 5;
c) SEQ ID NO: 7;
d) or any coding sequence encoding a glutamate decarboxylase as defined above.

The present invention also relates to a glutamate decarboxylase enzyme as defined above; as well as to a nucleic acid sequence comprising the coding sequence for such a glutamate decarboxylase.

In another embodiment, the present invention provides an expression cassette, comprising at least one nucleic acid sequence as defined above, which sequence is operatively linked to at least one regulatory nucleic acid sequence; as well as a recombinant vector, comprising at least one such expression cassette.

The present invention also relates to a prokaryotic or eukaryotic host, trans-formed with at least one vector as defined above; in particular to hosts selected from recombinant coryneform bacteria, especially a recombinant *Corynebacterium*, as, for example, recombinant *Corynebacterium glutamicum*.

Finally, the present invention relates to a method of preparing a polymer, in particular, a polyamide, which method comprises a) preparing GABA by a method as described above;
b) isolating GABA; and
c) polymerizing said GABA, optionally in the presence of at least one further suitable polyvalent copolymerizable co-monomer, selected, for example, from aminocarboxylic acids and hydroxycarboxylic acids.

2. Explanation of Particular Terms

Unless otherwise stated the expressions "gamma-aminobutyric acid", "gammaaminobutyrate" and "GABA" are considered to be synonymous. The GABA product as obtained according to the present invention may be in the form of the free acid, in the form of a partial or complete salt of said acid and base functional groups or in the form of mixtures of the non-charged acid and any of its salt or mixtures.

A GABA "salt" comprises for example metal salts, as for example mono- or dialkalimetal salts of GABA like monosodium di-sodium, mono-potassium and dipotassium salts as well as alkaline earth metal salts as for example the calcium or magnesium salts or the protonated form of GABA.

"Deregulation" has to be understood in its broadest sense, and comprises an increase or decrease of complete switch off of an enzyme (target enzyme) activity by different means well known to those in the art. Suitable methods comprise for example an increase or decrease of the copy number of gene and/or enzyme molecules in an organism, or the modification of another feature of the enzyme affecting the its enzymatic activity, which then results in the desired effect on the metabolic pathway at issue, in particular the Glutamate biosynthetic pathway or any pathway or enzymatic reaction coupled thereto. Suitable genetic manipulation can also include, but is not limited to, altering or modifying regulatory sequences or sites associated with expression of a particular gene (e.g., by removing strong promoters, inducible promoters or multiple promoters), modifying the chromosomal location of a particular gene, altering nucleic acid sequences adjacent to a particular gene such as a ribosome binding site or transcription terminator, decreasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, or other methods to knock-out or block expression of the target protein).

The term "heterologous" or "exogenous" refers to proteins, nucleic acids and corresponding sequences as described herein, which are introduced into or produced (transcribed or translated) by a genetically manipulated microorganism as defined herein and which microorganism prior to said manipulation did not contain or did not produce said sequence. In particular said microorganism prior to said manipulation may not contain or express said heterologous enzyme activity, or may contain or express an endogenous enzyme of comparable activity or specificity, which is encoded by a different coding sequence or by an enzyme of different amino acid sequence, and said endogenous enzyme may convert the same substrate or substrates as said exogenous enzyme.

A "parent" microorganism of the present invention is any microorganism having the ability to produce glutamate.

A microorganism "derived from a parent microorganism" refers to a microorganism modified by any type of manipulation, selected from chemical, biochemical or microbial, in particular genetic engineering techniques. Said manipulation results in at least one change of a biological feature of said parent microorganism. As an example the coding sequence of a heterologous enzyme may be introduced into said organism. By said change at least one feature may be added to, replaced in or deleted from said parent microorganism. Said change may, for example, result in an altered metabolic feature of said microorganism, so that, for example, a substrate of an enzyme expressed by said microorganism (which substrate was not utilized at all or which was utilized with different efficiency by said parent microorganism) is metabolized in a characteristic way (for example, in different amount, proportion or with different efficiency if compared to the parent microorganism), and/or a metabolic final or intermediary product is formed by said modified microorganism in a characteristic way (for example, in different amount, proportion or with different efficiency if compared to the parent microorganism).

An "intermediary product" is understood as a product, which is transiently or continuously formed during a chemical or biochemical process, in a not necessarily analytically directly detectable concentration. Said "intermediary product" may be removed from said biochemical process by a second, chemical or biochemical reaction, in particular by a reaction catalyzed by a "glutamate decarboxylase" enzyme as defined herein.

The term "glutamate decarboxylase" refers to any enzyme of any origin having the ability to convert glutamate into GABA. Such enzymes are classified as EC. 4.1.1.15.

A "recombinant host" may be any prokaryotic or eukaryotic cell, which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., MOLECULAR CLONING: A LABORATORY MANUAL, Second Edition, Cold Spring Harbor Laboratory, Cold Spring Harbor, N.Y. (1989).

The term "recombinant microorganism" includes a microorganism (e.g., bacteria, yeast, fungus, etc.) or microbial strain, which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturallyoccurring microorganism or "parent" microorganism which it was derived from.

As used herein, a "substantially pure" protein or enzyme means that the desired purified protein is essentially free from contaminating cellular components, as evidenced by a single band following polyacrylamide-sodium dodecyl sulfategel electrophoresis (SDS-PAGE). The term "substantially pure" is further meant to describe a molecule, which is homogeneous by one or more purity or homogeneity characteristics used by those of skill in the art. For example, a substantially pure glutamate decarboxylase will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of glutamate decarboxylase with other compounds. In addition, the term is not meant to exclude glutamate decarboxylase fusion proteins optionally isolated from a recombinant host.

3. Other Embodiments of the Invention 3.1 Deregulation of further genes

The fermentative production of GABA with a recombinant *Corynebacterium glutamate* producer expressing glutamate decarboxylase may be further improved if it is combined with the deregulation of at least one further gene as listed below.

| Enzyme (gene product) | Gene | Deregulation |
|---|---|---|
| isocitrate dehydrogenase | icd NCgl0634 | amplification |
| glutamate dehydrogenase | gdh NCgl1999 | amplification |
| phosphoenolpyruvate carboxylase | ppc NCgl1523 | amplification |
| pyruvate carboxylase | pycA NCgl0659 | Releasing feedback inhibition by point mutation (EP1108790) and amplification |
| 2-oxoglutarate dehydrogenase | odhA NCgl1084 | attenuation (WO2006/028298) |
| isocitrate lyase | aceA NCgl2248 | attenuation |
| phosphoenolpyruvate carboxykinase | pck NCgl2765 | attenuation |
| glutamine synthetase | glnA NCgl2148 | attenuation |
| glutamate exporter | yggB NCgl1221 | attenuation (WO2006070944) |

A preferred way of an "amplification" is an "up"-mutation which increases the gene activity e.g. by gene amplification using strong expression signals and/or point mutations which enhance the enzymatic activity.

A preferred way of an "attenuation" is a "down"-mutation which decreases the gene activity e.g. by gene deletion or disruption, using weak expression signals and/or point mutations which destroy or decrease the enzymatic activity.

3.2 Proteins According to the Invention

The present invention is not limited to the specifically mentioned proteins, but also extends to functional equivalents thereof.

"Functional equivalents" or "analogs" or "functional mutations" of the concretely disclosed enzymes are, within the scope of the present invention, various polypeptides thereof, which moreover possess the desired biological function or activity, e.g. enzyme activity.

For example, "functional equivalents" means enzymes, which, in a test used for enzymatic activity, display at least a 1 to 10%, or at least 20%, or at least 50%, or at least 75%, or at least 90% higher or lower activity of an enzyme, as defined herein.

"Functional equivalents", according to the invention, also means in particular mutants, which, in at least one sequence position of the amino acid sequences stated above, have an amino acid that is different from that concretely stated, but nevertheless possess one of the aforementioned biological activities. "Functional equivalents" thus comprise the mutants obtainable by one or more amino acid additions, substitutions, deletions and/or inversions, where the stated changes can occur in any sequence position, provided they lead to a mutant with the profile of properties according to the invention. Functional equivalence is in particular also provided if the reactivity patterns coincide qualitatively between the mutant and the unchanged polypeptide, i.e. if for example the same substrates are converted at a different rate. Examples of suitable amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" that are also included according to the invention are homologues of the concretely disclosed proteins. These possess percent identity values as stated above. Said values refer to the identity with the concretely disclosed amino acid sequences, and may be calculated according to the algorithm of Pearson and Lipman, Proc. Natl. Acad, Sci. (USA) 85(8), 1988, 2444-2448. The % identity values may also be calculated from BLAST alignments, algorithm blastp (protein-protein BLAST) or by applying the Clustal setting as given below.

A percentage identity of a homologous polypeptide according to the invention means in particular the percentage identity of the amino acid residues relative to the total length of one of the amino acid sequences concretely described herein.

In the case of a possible protein glycosylation, "functional equivalents" according to the invention comprise proteins of the type designated above in deglycosylated or glycosylated form as well as modified forms that can be obtained by altering the glycosylation pattern.

Such functional equivalents or homologues of the proteins or polypeptides according to the invention can be produced by mutagenesis, e.g. by point mutation, lengthening or shortening of the protein.

Such functional equivalents or homologues of the proteins according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992) PNAS 89:7811-7815; Delgrave et al. (1993) Protein Engineering 6(3):327-331).

3.3 Coding Nucleic Acid Sequences

The invention also relates to nucleic acid sequences that code for enzymes as defined herein.

The present invention also relates to nucleic acids with a certain degree of "identity" to the sequences specifically disclosed herein. "Identity" between two nucleic acids means identity of the nucleotides, in each case over the entire length of the nucleic acid.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple alignment parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13): 3497-500, the web page: ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The invention also relates to nucleic acid sequences (single-stranded and double-stranded DNA and RNA sequences, e.g. cDNA and mRNA), coding for one of the above polypeptides and their functional equivalents, which can be obtained for example using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for identifying or amplifying coding nucleic acids according to the invention.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (see below) on at least about 12, preferably at least about 25, for example about 40, 50 or 75 successive nucleotides of a sense strand of a nucleic acid sequence according to the invention or of a corresponding antisense strand.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These standard conditions vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1× SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular be carried out under stringent conditions. Such hybridization conditions are for example described in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM tri-sodium citrate), 50 mM sodium phosphate (pH 7.6), 5×Denhardt Solution, 10% dextran sulfate and 20 g/ml denatured, sheared salmon sperm DNA, followed by washing of the filters with 0.1×SSC at 65° C.

The invention also relates to derivatives of the concretely disclosed or derivable nucleic acid sequences.

Thus, further nucleic acid sequences according to the invention can be derived from the sequences specifically disclosed herein and can differ from it by addition, substitution, insertion or deletion of individual or several nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism, as well as naturally occurring variants, e.g. splicing variants or allelic variants, thereof.

It also relates to sequences that can be obtained by conservative nucleotide substitutions (i.e. the amino acid in question is replaced by an amino acid of the same charge, size, polarity and/or solubility).

The invention also relates to the molecules derived from the concretely disclosed nucleic acids by sequence polymorphisms. These genetic polymorphisms can exist between individuals within a population owing to natural variation. These natural variations usually produce a variance of 1 to 5% in the nucleotide sequence of a gene.

Derivatives of nucleic acid sequences according to the invention mean for example allelic variants, having at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

Furthermore, derivatives are also to be understood to be homologues of the nucleic acid sequences according to the invention, for example animal, plant, fungal or bacterial homologues, shortened sequences, single-stranded DNA or RNA of the coding and noncoding DNA sequence. For example, homologues have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

3.4 Constructs According to the Invention

The invention also relates to expression constructs, containing, under the genetic control of regulatory nucleic acid sequences, a nucleic acid sequence coding for a polypeptide or fusion protein according to the invention; as well as vectors comprising at least one of these expression constructs.

"Expression unit" means, according to the invention, a nucleic acid with expression activity, which comprises a promoter as defined herein and, after functional association with a nucleic acid that is to be expressed or a gene, regulates the expression, i.e. the transcription and the translation of this nucleic acid or of this gene. In this context, therefore, it is also called a "regulatory nucleic acid sequence". In addition to the promoter, other regulatory elements may be present, e.g. enhancers.

"Expression cassette" or "expression construct" means, according to the invention, an expression unit, which is functionally associated with the nucleic acid that is to be expressed or the gene that is to be expressed. In contrast to an expression unit, an expression cassette thus comprises not only nucleic acid sequences which regulate transcription and translation, but also the nucleic acid sequences which should be expressed as protein as a result of the transcription and translation.

The terms "expression" or "overexpression" describe, in the context of the invention, the production or increase of intracellular activity of one or more enzymes in a microorganism, which are encoded by the corresponding DNA. For this, it is possible for example to insert a gene in an organism, replace an existing gene by another gene, increase the number of copies of the gene or genes, use a strong promoter or use a gene that codes for a corresponding enzyme with a high activity, and optionally these measures can be combined.

Preferably such constructs according to the invention comprise a promoter 5'-upstream from the respective coding sequence, and a terminator sequence 3'-downstream, and optionally further usual regulatory elements, in each case functionally associated with the coding sequence.

A "promoter", a "nucleic acid with promoter activity" or a "promoter sequence" mean, according to the invention, a nucleic acid which, functionally associated with a nucleic acid that is to be transcribed, regulates the transcription of this nucleic acid.

"Functional" or "operative" association means, in this context, for example the sequential arrangement of one of the nucleic acids with promoter activity and of a nucleic acid sequence that is to be transcribed and optionally further regulatory elements, for example nucleic acid sequences that enable the transcription of nucleic acids, and for example a terminator, in such a way that each of the regulatory elements can fulfill its function in the transcription of the nucleic acid sequence. This does not necessarily require a direct association in the chemical sense. Genetic control sequences, such as enhancer sequences, can also exert their function on the target sequence from more remote positions or even from other DNA molecules. Arrangements are preferred in which the nucleic acid sequence that is to be transcribed is positioned behind (i.e. at the 3' end) the promoter sequence, so that the two sequences are bound covalently to one another. The distance between the promoter sequence and the nucleic acid sequence that is to be expressed transgenically can be less than 200 bp (base pairs), or less than 100 bp or less than 50 bp.

Apart from promoters and terminators, examples of other regulatory elements that may be mentioned are targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise in particular sequences selected from those, specifically mentioned herein or derivatives and homologues thereof, as well as the nucleic acid sequences that can be derived from amino acid sequences specifically mentioned herein which are advantageously associated operatively or functionally with one or more regulating signal for controlling, e.g. increasing, gene expression.

In addition to these regulatory sequences, the natural regulation of these sequences can still be present in front of the actual structural genes and optionally can have been altered genetically, so that natural regulation is switched off and the expression of the genes has been increased. The nucleic acid construct can also be of a simpler design, i.e. without any additional regulatory signals being inserted in front of the coding sequence and without removing the natural promoter with its regulation. Instead, the natural regulatory sequence is silenced so that regulation no longer takes place and gene expression is increased.

A preferred nucleic acid construct advantageously also contains one or more of the aforementioned enhancer sequences, functionally associated with the promoter, which permit increased expression of the nucleic acid sequence. Additional advantageous sequences, such as other regulatory elements or terminators, can also be inserted at the 3' end of the DNA sequences. One or more copies of the nucleic acids according to the invention can be contained in the construct. The construct can also contain other markers, such as antibiotic resistances or auxotrophycomplementing genes, optionally for selection on the construct.

Examples of suitable regulatory sequences are contained in promoters such as cos-, tac-, trp-, tet-, trp-tet-, lpp-, lac-, lpp-lac-, lacI$^{q-}$ T7-, T5-, T3-, gal-, trc-, ara-, rhaP (rhaP$_{BAD}$) SP6-, lambda-P$_R$- or in the lambda-P$_L$ promoter, which find application advantageously in Gram-negative bacteria. Other advantageous regulatory sequences are contained for example in the Gram-positive promoters ace, amy and SPO2, in the yeast or fungal promoters ADC1, MFalpha, AC, P-60, CYC1, GAPDH, TEF, rp28, ADH. Artificial promoters can also be used for regulation.

For expression, the nucleic acid construct is inserted in a host organism advantageously in a vector, for example a plasmid or a phage, which permits optimum expression of the genes in the host. In addition to plasmids and phages, vectors are also to be understood as meaning all other vectors known to a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are, for example in *E. coli*, pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI; in nocardioform actinomycetes pJAM2; in *Streptomyces* pIJ101, pIJ364, pIJ702 or pIJ361; in *bacillus* pUB110, pC194 or pBD214; in *Corynebacterium* pSA77 or pAJ667; in fungi pALS1, pIL2 or pBB116; in yeasts 2alphaM, pAG-1, YEp6, YEp13 or pEMBLYe23 or in plants pLGV23, pGHlac$^+$, pBIN19, pAK2004 or pDH51. The aforementioned plasmids represent a small selection of the possible plasmids. Other plasmids are well known to a person skilled in the art and will be found for example in the book Cloning Vectors (Eds. Pouwels P. H. et al. Elsevier, Amsterdam-N.Y.-Oxford, 1985, ISBN 0 444 904018).

In a further embodiment of the vector, the vector containing the nucleic acid construct according to the invention or the nucleic acid according to the invention can be inserted advantageously in the form of a linear DNA in the microorganisms and integrated into the genome of the host organism through heterologous or homologous recombination. This linear DNA can comprise a linearized vector such as plasmid or just the nucleic acid construct or the nucleic acid according to the invention.

For optimum expression of heterologous genes in organisms, it is advantageous to alter the nucleic acid sequences in accordance with the specific codon usage employed in the organism. The codon usage can easily be determined on the basis of computer evaluations of other, known genes of the organism in question.

The production of an expression cassette according to the invention is based on fusion of a suitable promoter with a suitable coding nucleotide sequence and a terminator signal or polyadenylation signal. Common recombination and cloning techniques are used for this, as described for example in T. Maniatis, E. F. Fritsch and J. Sambrook, Molecular Cloning: A Laboratory Manual, Cold Spring Harbor Laboratory, Cold Spring Harbor, N.Y. (1989) as well as in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is inserted advantageously in a host-specific vector for expression in a suitable host organism, to permit optimum expression of the genes in the host. Vectors are well known to a person skilled in the art and will be found for example in "Cloning Vectors" (Pouwels P. H. et al., Publ. Elsevier, Amsterdam-N.Y.-Oxford, 1985).

3.5 Hosts that can be Used According to the Invention

Depending on the context, the term "microorganism" means the starting microorganism (wild-type) or a genetically modified microorganism according to the invention, or both.

The term "wild-type" means, according to the invention, the corresponding starting microorganism, and need not necessarily correspond to a naturally occurring organism.

By means of the vectors according to the invention, recombinant microorganisms can be produced, which have been transformed for example with at least one vector according to the invention and can be used for the fermentative production according to the invention.

Advantageously, the recombinant constructs according to the invention, described above, are inserted in a suitable host system and expressed. Preferably, common cloning and transfection methods that are familiar to a person skilled in the art are used, for example co-precipitation, protoplast fusion, electroporation, retroviral transfection and the like, in order to secure expression of the stated nucleic acids in the respective expression system. Suitable systems are described for example in Current Protocols in Molecular Biology, F. Ausubel et al., Publ. Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

The parent microorganisms ate typically those which have the ability to produce lysine, in particular L-lysine, from glucose, saccharose, lactose, fructose, maltose, molassis, starch, cellulose or glycerol, fatty acids, plant oils or ethanol. Preferably they are coryneform bacteria, in particular of the genus *corynebacterium* or of the genus *Brevibacterium*. In particular the species *Corynebacterium glutamicum* has to be mentioned.

Non-limiting examples of suitable strains of the genus *Corynebacterium*, and the species *Corynebacterium glutamicum* (*C. glutamicum*), are
*Corynebacterium glutamicum* ATCC 13032,
*Corynebacterium acetoglutamicum* ATCC 15806,
*Corynebacterium acetoacidophilum* ATCC 13870,
*Corynebacterium thermoaminogenes* FERM BP-1539,
*Corynebacterium melassecola* ATCC 17965
and of the genus *Brevibacterium*, are
*Brevibacterium flavum* ATCC 14067
*Brevibacterium lactofermentum* ATCC 13869 and
*Brevibacterium divaricatum* ATCC 14020
or strains derived there from like,
*Corynebacterium glutamicum* KFCC10065
*Corynebacterium glutamicum* ATCC21608

KFCC designates Korean Federation of Culture Collection, ATCC designates American type strain culture collection, FERM BP designates the collection of National institute of Bioscience and Human-Technology, Agency of Industrial Science and Technology, Japan.

The host organism or host organisms according to the invention preferably contain at least one of the nucleic acid sequences, nucleic acid constructs or vectors described in this invention, which code for an enzyme activity according to the above definition.

3.5 Fermentative Production of GABA

The invention also relates to methods for the fermentative production of GABA.

The recombinant microorganisms as used according to the invention can be cultivated continuously or discontinuously in the batch process or in the fed batch or repeated fed batch process. A review of known methods of cultivation will be found in the textbook by Chmiel (Bioprocesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention generally comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 10 hours to 160 hours.

The cells can be disrupted optionally by high-frequency ultrasound, by high pressure, e.g. in a French pressure cell, by osmolysis, by the action of detergents, lytic enzymes or organic solvents, by means of homogenizers or by a combination of several of the methods listed.

3.6 GABA Isolation

The methodology of the present invention can further include a step of recovering GABA. The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. For example GABA can be recovered from culture media by first removing the microorganisms. The remaining broth is then passed through or over a cation exchange resin to remove unwanted cations and then through or over an anion exchange resin to remove unwanted inorganic anions and organic acids.

3.7 Polyamide Polymers and Pyrrolidone

In another aspect, the present invention provides a process for the production of polymers, in particular polyamides, comprising a step as mentioned above for the production of GABA. The GABA is reacted in a known manner with itself or at least one different co-monomer, selected from amino- and hydroxycarboxylic acids by applying standard methods of polymer synthesis. Suitable co-monomers are for example derived from $C_2$-$C_{31}$, preferably $C_4$-$C_{10}$-straight or branched chain monocarboxylic acids, carrying at least one reactive hydroxyl or amino group.

Such hydroxyl- or amino-substituted, copolymerizable "carboxylic acids" are derived from straight-chain or branched, saturated or mono- or poly-unsaturated $C_2$-$C_{30}$-monocarboxylic acids. In particular, said acids carry a straight-chain mono- or poly-unsaturated hydrocarbyl residue or a mixture of such residues with an average length of 1-30, preferably 3-9 carbon atoms. Particularly preferred residues are:

saturated, straight-chain residues like $CH_3$—, $C_2H_5$—; $C_3H_7$—; $C_4H_9$—; $C_5H_{11}$—; $C_6H_{13}$—; $C_7H_{15}$—, $C_8H_{17}$—; $C_9H_{19}$—; $C_{10}H_{21}$—; $C_{11}H_{23}$—; $C_{12}H_{25}$—; $C_{13}H_{27}$—; $C_{14}H_{29}$—; $C_{15}H_{31}$—; $C_{16}H_{33}$—; $C_{17}H_{35}$—; $C_{18}H_{37}$—; $C_{19}H_{39}$—; $C_{20}H_{41}$—; $C_{21}H_{43}$—; $C_{23}H_{47}$—; $C_{24}H_{49}$; —$C_{25}H_{51}$—; $C_{29}H_{59}$—; $C_{30}H_{61}$;

saturated, branched residues like iso-$C_3H_7$—; iso-$C_4H_9$—; iso-$C_{15}H_{37}$—;

mono-unsaturated, straight-chain residues like $C_2H_3$—; $C_3H_5$—; $C_{15}H_{29}$—; $C_{17}H_{33}$—; $C_{21}H_{41}$—;

two-fold unsaturated, straight-chain like $C_5H_7$—; $C_{17}H_{31}$—;

Those residues are modified so that they carry alt least one functional substituent, selected from hydroxyl and amino groups, required for copolymerization.

In another aspect the fermentatively produced GABA may be applied for producing pyrrolidone by applying standard techniques of organic synthesis.

The following examples only serve to illustrate the invention. The numerous possible variations that are obvious to a person skilled in the art also fall within the scope of the invention.

EXPERIMENTAL PART

Unless otherwise stated the following experiments have been performed by applying standard equipment, methods, chemicals, and biochemicals as used in genetic engineering, fermentative production of chemical compounds by cultivation of microorganisms and in the analysis and isolation of products. See also Sambrook et al, and Chmiel et al as cited herein above.

Example 1

Cloning of an *E. coli* Glutamate Decarboxylase (GAD) Gene

Figure 3:
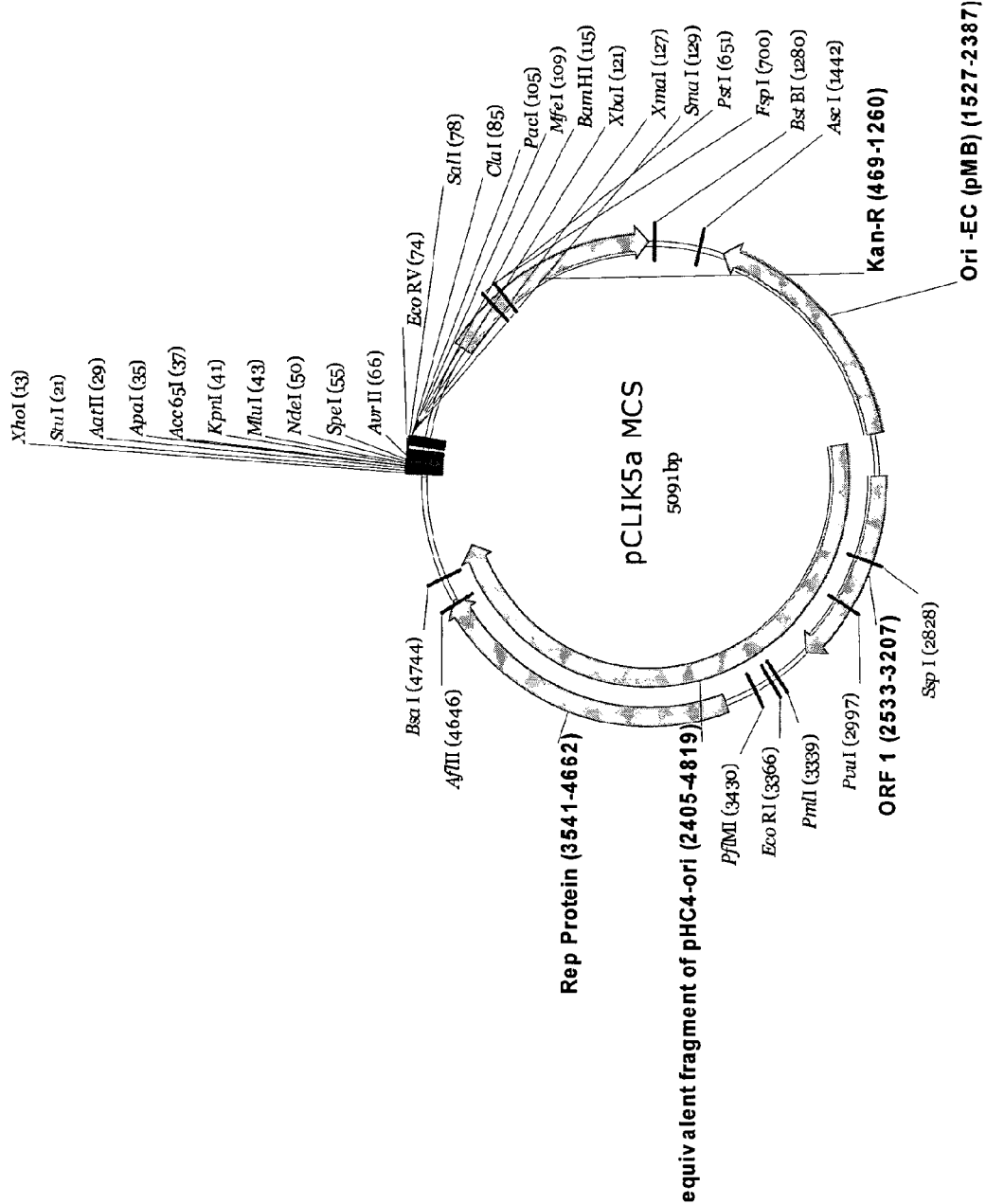
FIG. 3 depicts the plasmid map of the pClik5aMCS cloning vector.

PCR primers, WKJ95/WKJ96 and WKJ99/WKJ100, were used with chromosomal DNA of *E. coli* as a template to amplify the DNA fragments containing the gadBC and gadA genes, respectively. The amplified DNA fragments were purified, digested with restriction enzymes, XhoI/XbaI for gadBC and XhoI/SpeI for gadA, and ligated to the pClik5aMCS (SEQ ID NO:14; FIG. 3) vector digested with same restriction enzymes resuiting in pClik5aMCS gadBC and pClik5aMCS gadA, respectively.

Oligonucleotide primers used:

```
WKJ95
                                        (SEQ ID NO: 10)
ccgctcgagcggcccaagcttcggtaaatacttataccggag WKJ96
                                        (SEQ ID NO: 11)
ctagtctagactagcccaagcttgtcgatcatcgcctgttg WKJ99
                                        (SEQ ID NO: 12)
ccgctcgagcggcccaagcttcgtgataaattgcgtcagaaag WKJ100
                                        (SEQ ID NO: 13)
ctagactagtctagcccaagcttctcgaatttggcttgcatcc
```

Example 2

Search for GAD Gene in *Solanum tuberosum* (Potato)

In order to find a yet unknown gene that encodes GAD in potato, the first step was to identify a GAD from a closely related organism. A query in the sequence databases Genbank, Refseq and Uniprot for "glutamate decarboxlase" in the genus "*Solanum*" revealed a previously characterised GAD in *Solanum lycopersicum* (tomato), Swissprot accession number P54767. This sequence was used as a template to perform a tblastn search in Genbank subsections plant, EST and GSS. Among the best 100 hits (expect value $<10^{-118}$) 16 sequences were extracted from *Solanum tuberosum* (potato). All 16 sequences are expressed sequence tags (EST), i.e. represent fragments of the expressed and spliced mRNAs. An assembly using VectorNTl Contig Express (settings: overlap=20, identity=0.8, cut-off score=40) revealed a contig composed of 15 sequences and a second contig made up by one sequence (BG594946).

To check the quality of the assembly and to make a decision, which of the contigs to choose, the consensus sequences of both assemblies were generated and compared with all 100 hits from the initial blast search. The alignment (shown as guide tree in FIG. 1) revealed contig 1 to be an outlier. Since contig 2 that is composed solely of the EST with the accession BG594946 fits very well to the tomato GAD, it was chosen as the best candidate to represent the potato GAD.

Figure 2:
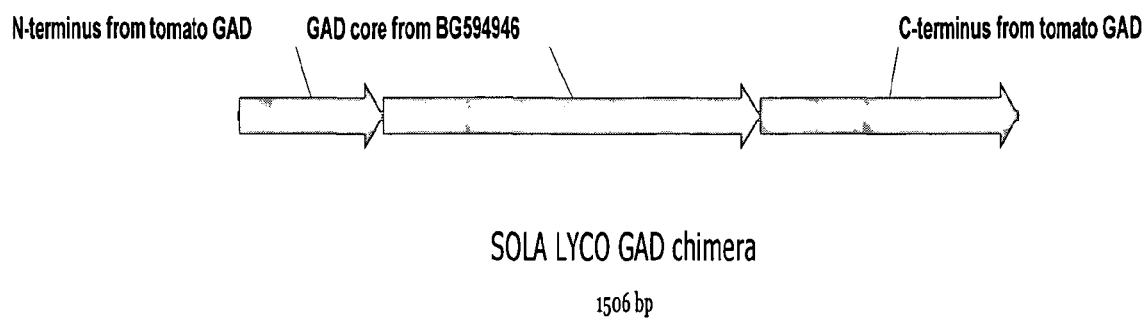
FIG. 2 depicts the schematic drawing of a chimera GAD gene of the invention.

Since BG594946 only covers the core of the GAD gene, the flanking 5' and 3' regions were taken from the corresponding tomato gene resulting in a chimera GAD gene as shown in FIG. 2.

Example 3

Cloning of a Synthetic Chimera GAD Gene

As the codon usage for the plant-originated chimera GAD gene is quite different to that of the *C. glutamicum* genes, expression of the chimera GAD gene may not be efficient in a *C. glutamicum* strain. To enhance gene expression in *C. glutamicum*, a synthetic GAD gene with the sequence being adapted to *C. glutamicum* codon usage was created on the basis of the chimera GAD gene without a calmodulin binding sequence. Furthermore, the synthetic GAD gene had a *C. glutamicum* sodA promoter (Psod) and a groEL terminator. The synthetic GAD gene was digested with restriction enzyme SpeI and inserted to the pClik5aMCS vector digested with the same restriction enzyme resulting in pClik5aMCS Psod SL_gad.

Example 4

GABA Production in Shake Flask Culture

To construct a GABA production strain glutamate producing bacterium *C. glutamicum* ATCC13032 was transformed with the recombinant plasmids containing the GAD genes.

Shaking flask experiments were performed on the recombinant strains to test the GABA production. The strains were pre-cultured on CM plates (10 g/l glucose, 2.5 g/l NaCl, 2 g/l urea, 10 g/l Bacto peptone, 10 g/l yeast extract, 22 g/l agar) overnight at 30° C. Cultured cells were harvested in a microtube containing 1.5 ml of 0.9% NaCl and cell density was determined by the absorbance at 610 nm following vortex.

For the main culture suspended cells were inoculated to reach 1.5 of initial OD into 10 ml of the production medium (60 g/l glucose, 30 g/l $(NH_4)_2SO_4$, 2 g/l yeast extract, 1 g/l $KH_2PO_4$, 1 g/l $MgSO_4.7H_2O$, 10 mg/l $FeSO_4.7H_2O$, 10 mg/l $MnSO_4.H_2O$, 0.2 mg/l thiamine.HCl, 2 mg/l biotin, 52 g/l ACES, pH 6.5) contained in an autoclaved 100 ml of Erlenmeyer flask. Main culture was performed on a rotary shaker (Infors AJ118, Bottmingen, Switzerland) with 200 rpm for 48 hours at 30° C. The determination of the GABA concentration was conducted by HPLC (Agilent 1100 Series) with a Gemini C18 column (Phenomenex) and a fluorescence detector (Agilent). A pre-column derivatization with ortho-phthalaldehyde allows the quantification of GABA. Cell growth was monitored by a spectrophotometer at 610 nm.

An accumulation of GABA was observed in all recombinant strains containing the GAD gene. The recombinant strain carrying the pClik5aMCS Psod SL_gad plasmid showed the highest GABA productivity. The results are summarized in following table:

TABLE

| GABA production in shaking flask culture | |
|---|---|
| Strains | GABA (mmol/g cell) |
| ATCC13032 | 0.0 |
| +pClik5aMCS | 0.0 |
| +pClik5aMCS gadA | 0.2 |
| +pClik5aMCS gadBC | 0.4 |
| +pClik5aMCS Psod SL_gad | 1.2 |

Any document cited herein is incorporated by reference.

The invention claimed is:

1. A method for the fermentative production of gamma-aminobutyric acid (GABA), comprising cultivating a recombinant microorganism derived from a parent microorganism having the ability to produce glutamate and additionally having the ability to express a heterologous glutamate decarboxylase (E.C. 4.1.1.15) in a culture medium, wherein said microorganism is a *Corynebacterium*, wherein glutamate is converted to GABA in said recombinant microorganism, and wherein said heterologous glutamate decarboxylase is encoded by a nucleic acid composing:
  a) the nucleotide sequence from position 472 to 1200 of SEQ ID NO: 1 or from position 193 to 1605 of SEQ ID NO: 1;
  b) a nucleotide sequence encoding a glutamate decarboxylase comprising the amino acid sequence of SEQ ID NO: 2; or
  c) a nucleotide sequence encoding a glutamate decarboxylase comprising an amino acid sequence having at least 95% sequence identity to SEQ ID NO: 2, wherein said glutamate decarboxylase comprises the amino acid sequence from Thr94 to Leu336 of SEQ ID NO: 2 or an amino acid sequence having at least 98% sequence identity to the amino acid sequence from Thr94 to Leu336 of SEQ ID NO: 2.

2. The method of claim 1, wherein the microorganism is *Corynebacterium glutamicum*.

3. The method of claim 1, wherein said heterologous glutamate decarboxylase is of eukaryotic origin.

4. The method of claim 1, wherein said heterologous glutamate decarboxylase is a plant glutamate decarboxylase or a chimeric glutamate decarboxylase comprising at least one amino acid sequence portion obtained from a plant glutamate decarboxylase.

5. The method of claim 4, wherein said plant glutamate decarboxylase is obtained from a plant of the genus *Solanum*, from *Solanum tuberosum*, or from *Solanum lycopersicum*.

6. The method of claim 1, wherein the heterologous glutamate decarboxylase comprises the amino acid sequence from Thr94 to Leu336 of SEQ ID NO: 2 or an amino acid sequence having at least 98% sequence identity to the amino acid sequence from Thr94 to Leu336 of SEQ ID NO: 2.

7. The method of claim 1, wherein, the heterologous glutamate decarboxylase is a chimeric glutamate decarboxylase comprising the amino acid sequence from Thr94 to Leu336 of SEQ ID NO: 2 or an amino acid sequence having at least 95% sequence identity thereto, wherein said chimeric glutamate decarboxylase further comprises at least one ammo acid sequence portion at the N-terminus, the C-terminus, or both the N-terminus and C-terminus, of said amino acid sequence from Thr94 to Leu336 of SEQ ID NO: 2 or an amino acid sequence having at least 95% sequence identity thereto, and wherein the at least one amino acid sequence portion is obtained from it corresponding amino acid sequence portion of a glutamate decarboxylase of *Solanum tuberosum* or a plant different from *Solanum tuberosum*.

8. The method of claim 7, wherein aid plant different from *Solanum tuberosum* is *Solanum lycopersicum*.

9. The method of claim 1, wherein said heterologous glutamate decarboxylase comprises the amino acid sequence of SEQ ID NO: 2 or is encoded by the nucleotide sequence from position 472 to 1200 of SEQ ID NO: 1 or from position 193 to 1605 of SEQ ID NO: 1.

10. The method of claim 1, wherein the heterologous glutamate decarboxylase is encoded by a nucleic acid sequence adapted to the codon usage of *Corynebacterium*.

11. A chimeric glutamate decarboxylase comprising the amino acid sequence from Thr94 to Leu336 of SEQ ID NO: 2 or an amino acid sequence having at least 95% sequence identity thereto, wherein said chimeric glutamate decarboxylase further comprises at least one amino acid sequence portion at the N-terminus, the C-terminus, or both the N-terminus and C-terminus, of said amino acid sequence from Thr94 to Leu336 of SEQ ID NO: 2 or an amino acid sequence having at least 95% sequence identity thereto, wherein the at least one amino acid sequence portion is obtained from a corresponding amino acid sequence portion of a glutamate decarboxylase of a plant different from *Solanum tuberosum*, and wherein said chimeric glutamate decarboxylase encoded by a nucleic acid comprising:
   a) the nucleotide sequence from position 472 to 1200 of SEQ ID NO: 1 or from position 193 to 1605 of SEQ ID NO: 1;
   b) a nucleotide sequence encoding a glutamate decarboxylase comprising the amino acid sequence of SEQ ID NO: 2; or
   c) a nucleotide sequence encoding a glutamate decarboxylase comprising an amino acid sequence having at least 95% sequence identity to SEQ ID NO: 2, wherein said glutamate decarboxylase comprises the amino acid sequence from Thr94 to Leu336 of SEQ ID NO: 2 or an amino acid sequence having at least 98% sequence identity to the amino acid sequence from Thr94 to Leu336 of SEQ ID NO: 2.

12. An isolated nucleic acid molecule encoding the chimeric glutamate decarboxylase of claim 11.

13. An expression cassette comprising the isolated nucleic acid molecule of claim 12 operatively linked to at least one regulatory nucleic acid sequence.

14. A recombinant vector comprising at least one expression cassette of claim 13.

15. A prokaryotic host transformed with the recombinant vector of claim 14.

16. The prokaryotic host of claim 15, wherein the prokaryotic host is a recombinant *Corynebacterium*.

17. The prokaryotic host of claim 16, wherein the prokaryotic host is recombinant *Corynebacterium glutamicum*.

18. The method of claim 1, further comprising recovering the GABA produced from the culture medium.

19. A method of preparing, a polyamide comprising:
   a) preparing GABA by the method of claim 1;
   b) isolating GABA; and
   c) polymerizing said GABA, optionally in the presence of at least one further suitable polyvalent co-monomer, selected from aminocarboxylic acids and hydroxycarboxylic acids.

20. The chimeric glutamate decarboxylase of claim 11, wherein said plant different from *Solanum tuberosum* is *Solanum lycopersicum*.

21. A method for the fermentative production of gamma-aminobutyric acid (GABA), comprising cultivating a recombinant microorganism derived from a parent microorganism having the ability to produce glutamate and additionally having the ability to express a heterologous glutamate decarboxylase (E.C. 4.1.1.15) in a culture medium, wherein said microorganism is a *Corynebacterium*, wherein glutamate is converted to GABA in said recombinant microorganism, and wherein said heterologous glutamate decarboxylase is encoded by a nucleotide sequence which hybridizes to the complementary sequence of the nucleotide sequence from position 472 to 1200 of SEQ ID NO: 1 or from position 193 to 1605 of SEQ ID NO: 1 under stringent hybridization conditions comprising hybridization at 42°C in a solution consisting of 50% formamide, 5×SSC, 50mM sodium phosphate, 5×Denhardt Solution, 10% dextran sulfate and 20g/ml denatured, sheared salmon sperm DNA, followed by washing with 0.1×SSC at 65°C.

* * * * *